(12) United States Patent
Schmidt et al.

(10) Patent No.: US 7,547,904 B2
(45) Date of Patent: Jun. 16, 2009

(54) SENSING PHOTON ENERGIES EMANATING FROM CHANNELS OR MOVING OBJECTS

(75) Inventors: Oliver Schmidt, Palo Alto, CA (US); Peter Kiesel, Palo Alto, CA (US); Noble M. Johnson, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 565 days.

(21) Appl. No.: 11/315,386

(22) Filed: Dec. 22, 2005

(65) Prior Publication Data

US 2007/0146704 A1 Jun. 28, 2007

(51) Int. Cl.
G01N 15/06 (2006.01)
G01N 21/49 (2006.01)
G01N 21/85 (2006.01)

(52) U.S. Cl. ..................................... 250/573
(58) Field of Classification Search ................ 250/573
See application file for complete search history.

(56) References Cited

U.S. PATENT DOCUMENTS

| | | |
|---|---|---|
| 2,708,389 A | 5/1955 | Kavanagh |
| 3,973,118 A | 8/1976 | LaMontagne |
| 4,081,277 A | 3/1978 | Brault et al. |
| 4,455,089 A | 6/1984 | Yeung et al. |
| 4,514,257 A | 4/1985 | Karlsson et al. |
| 4,573,796 A | 3/1986 | Martin et al. |
| 4,764,670 A | 8/1988 | Pace et al. |
| 4,957,371 A | 9/1990 | Pellicori et al. |
| 4,976,542 A | 12/1990 | Smith |
| 5,144,498 A | 9/1992 | Vincent |
| 5,166,755 A | 11/1992 | Gat |
| 5,305,082 A | 4/1994 | Bret |
| 5,324,401 A | 6/1994 | Yeung et al. |
| 5,370,842 A | 12/1994 | Miyazaki et al. |
| 5,414,508 A | 5/1995 | Takahashi et al. |
| 5,572,328 A | 11/1996 | Fouckhardt et al. |

(Continued)

FOREIGN PATENT DOCUMENTS

EP 1324018 A2 7/2003

(Continued)

OTHER PUBLICATIONS

Singh, K., Liu, C., Capjack, C., Rosmus, W., and Backhouse, C.J., "Analysis of cellular structure by light scattering measurements in a new cytometer design based on a liquid-core waveguide", IEEE Proc.-Nanobiotechnol., vol. 151, No. 1, Feb. 2004, pp. 10-16.

(Continued)

*Primary Examiner*—Seung C Sohn
(74) *Attorney, Agent, or Firm*—Leading-Edge Law Group, PLC; James T. Beran

(57) ABSTRACT

Photons emanating from a channel in a fluidic structure or from moving objects are sensed using a photosensor array in an integrated circuit. The array includes subrange cells that photosense within respective subranges of a photon energy range. For example, the subrange cells can receive photons in their respective subranges from a transmission structure that has laterally varying properties. The photons can be emitted in response to excitation or can be scattered in response to illumination.

34 Claims, 13 Drawing Sheets

U.S. PATENT DOCUMENTS

| | | | |
|---|---|---|---|
| 5,666,195 | A | 9/1997 | Shultz et al. |
| 5,682,038 | A | 10/1997 | Hoffman |
| 5,777,329 | A | 7/1998 | Westphal et al. |
| 5,784,507 | A | 7/1998 | Holm-Kennedy et al. |
| 5,792,663 | A | 8/1998 | Fry et al. |
| 5,793,485 | A | 8/1998 | Gourley |
| 5,801,831 | A | 9/1998 | Sargoytchev |
| 5,864,641 | A | 1/1999 | Murphy et al. |
| 5,872,655 | A | 2/1999 | Seddon et al. |
| 5,876,674 | A | 3/1999 | Dosoretz et al. |
| 5,880,474 | A | 3/1999 | Norton et al. |
| 5,945,676 | A | 8/1999 | Khalil et al. |
| 6,040,578 | A | 3/2000 | Malin et al. |
| 6,091,502 | A | 7/2000 | Weigl |
| 6,108,463 | A | 8/2000 | Herron et al. |
| 6,137,117 | A | 10/2000 | Feldstein et al. |
| 6,192,168 | B1 | 2/2001 | Feldstein et al. |
| 6,249,346 | B1 | 6/2001 | Chen et al. |
| 6,275,628 | B1 | 8/2001 | Jones et al. |
| 6,295,130 | B1 | 9/2001 | Sun et al. |
| 6,353,475 | B1 | 3/2002 | Jensen et al. |
| 6,399,405 | B1 | 6/2002 | Chen et al. |
| 6,405,073 | B1 | 6/2002 | Crowley et al. |
| 6,429,022 | B1 | 8/2002 | Kunz et al. |
| 6,459,080 | B1 | 10/2002 | Yin et al. |
| 6,483,959 | B1 | 11/2002 | Singh et al. |
| 6,490,034 | B1 | 12/2002 | Woias et al. |
| 6,505,775 | B1 | 1/2003 | Gu et al. |
| 6,519,037 | B2 | 2/2003 | Jung et al. |
| 6,525,308 | B1 | 2/2003 | Schmidt-Hattenberger |
| 6,558,945 | B1 | 5/2003 | Kao |
| 6,577,780 | B2 | 6/2003 | Lockhart |
| 6,580,507 | B2 | 6/2003 | Fry et al. |
| 6,603,548 | B2 | 8/2003 | Church et al. |
| 6,608,679 | B1 | 8/2003 | Chen et al. |
| 6,630,999 | B2 | 10/2003 | Shroder |
| 6,700,664 | B1 | 3/2004 | Honda et al. |
| 6,781,690 | B2 | 8/2004 | Armstrong et al. |
| 6,785,002 | B2 | 8/2004 | Zarrabian et al. |
| 6,800,849 | B2 | 10/2004 | Staats |
| 6,867,420 | B2 | 3/2005 | Mathies et al. |
| 6,870,149 | B2 | 3/2005 | Berezin |
| 6,887,713 | B2 | 5/2005 | Nelson et al. |
| 7,046,357 | B2 | 5/2006 | Weinberger et al. |
| 7,149,396 | B2 | 12/2006 | Schmidt et al. |
| 7,248,361 | B2 | 7/2007 | Kiesel et al. |
| 7,268,868 | B2 | 9/2007 | Kiesel et al. |
| 7,291,824 | B2 | 11/2007 | Kiesel et al. |
| 7,310,153 | B2 | 12/2007 | Kiesel et al. |
| 7,315,667 | B2 | 1/2008 | Schmidt et al. |
| 7,358,476 | B2 | 4/2008 | Kiesel et al. |
| 7,386,199 | B2 | 6/2008 | Schmidt et al. |
| 7,420,677 | B2 | 9/2008 | Schmidt et al. |
| 7,471,399 | B2 | 12/2008 | Kiesel et al. |
| 7,479,625 | B2 | 1/2009 | Kiesel et al. |
| 7,502,123 | B2 | 3/2009 | Schmidt et al. |
| 7,522,786 | B2 | 4/2009 | Kiesel et al. |
| 2002/0155485 | A1 | 10/2002 | Kao |
| 2003/0000835 | A1 | 1/2003 | Witt et al. |
| 2003/0020915 | A1 | 1/2003 | Schueller et al. |
| 2003/0077660 | A1 | 4/2003 | Pien et al. |
| 2003/0235924 | A1 | 12/2003 | Adams et al. |
| 2004/0027462 | A1 | 2/2004 | Hing |
| 2004/0031684 | A1 | 2/2004 | Witt |
| 2004/0032584 | A1 | 2/2004 | Honda et al. |
| 2004/0038386 | A1 | 2/2004 | Zesch et al. |
| 2004/0067167 | A1 | 4/2004 | Zhang et al. |
| 2004/0132214 | A1 | 7/2004 | Lin et al. |
| 2004/0141884 | A1 | 7/2004 | Unno et al. |
| 2004/0145738 | A1 | 7/2004 | Sun et al. |
| 2004/0175734 | A1 | 9/2004 | Stahler et al. |
| 2004/0223881 | A1 | 11/2004 | Cunningham et al. |
| 2005/0042615 | A1 | 2/2005 | Smith et al. |
| 2005/0068526 | A1 | 3/2005 | Avrutsky |
| 2005/0084203 | A1 | 4/2005 | Kane |
| 2005/0099624 | A1 | 5/2005 | Staehr et al. |
| 2005/0128479 | A1 | 6/2005 | Gilbert et al. |
| 2006/0039009 | A1 | 2/2006 | Kiesel et al. |
| 2006/0046312 | A1 | 3/2006 | Kiesel et al. |
| 2006/0092413 | A1 | 5/2006 | Kiesel et al. |
| 2006/0121555 | A1 | 6/2006 | Lean et al. |
| 2006/0138313 | A1 | 6/2006 | Tennant et al. |
| 2006/0182659 | A1 | 8/2006 | Unlu et al. |
| 2006/0268260 | A1 | 11/2006 | Liu et al. |
| 2006/0274313 | A1 | 12/2006 | Gilbert et al. |
| 2007/0070347 | A1 | 3/2007 | Scherer et al. |
| 2007/0076210 | A1 | 4/2007 | Kiesel et al. |
| 2007/0116609 | A1 | 5/2007 | Baeuerle et al. |
| 2007/0145236 | A1 | 6/2007 | Kiesel et al. |
| 2007/0145249 | A1 | 6/2007 | Kiesel et al. |
| 2007/0146888 | A1 | 6/2007 | Schmidt et al. |
| 2007/0147189 | A1 | 6/2007 | Schmidt et al. |
| 2007/0147726 | A1 | 6/2007 | Kiesel et al. |
| 2007/0147728 | A1 | 6/2007 | Schmidt et al. |
| 2007/0148760 | A1 | 6/2007 | Kiesel et al. |
| 2007/0201025 | A1 | 8/2007 | Greenwald |
| 2008/0013877 | A1 | 1/2008 | Schmidt et al. |
| 2008/0186504 | A1 | 8/2008 | Kiesel et al. |
| 2008/0197272 | A1 | 8/2008 | Kiesel et al. |

FOREIGN PATENT DOCUMENTS

| | | |
|---|---|---|
| EP | 1801562 A1 | 6/2007 |
| WO | WO 95/20144 | 7/1995 |
| WO | WO 99/44042 A2 | 9/1999 |
| WO | WO 00/62050 | 10/2000 |
| WO | WO 02/25269 A2 | 3/2002 |
| WO | WO 2004/083820 A2 | 9/2004 |
| WO | WO 2005/108963 A1 | 11/2005 |

OTHER PUBLICATIONS

Agilent Technologies, "Agilent 83453B High-Resolution Spectrometer—Technical Specifications", Feb. 2005, pp. 1-8.

Liu, G.L., and Lee, L.P., "Nanowell surface enhanced Raman scattering arrays fabricated by soft-lithography for label-free biomolecular detections in integrated microfluidics", Applied Physics Letters, vol. 87, 2005, pp. 1-3.

Devasenathipathy, S., and Santiago, J.G., "3 Electrokinetic Flow Diagnostics" in Breuer. K.S., Ed.. Micro-and Nano-Scale Diagnostic Techniques, Springer Verlag, New York, 2003, pp. 121-166.

Becker, H., and Gartner, C., "Polymer microfabrication methods for microfluidic analytical applications", Electrophoresis, vol. 21, 2000, pp. 12-26.

Jones, T.B., Gunji, M., Washizu, M., and Feldman, M.J., "Dielectrophoretic liquid actuation nanodroplet formation". Journal of Applied Physics, vol. 89, No. 2, 2001, pp. 1441-1448.

Amendment with Information Disclosure in U.S. Appl. No. 11/316,660, dated Jan. 17, 2008, 15 pages, published in PAIR.

Notice of Allowance and Fee(s) Due in U.S. Appl. No. 11/316,660, mailed Apr. 17, 2008, 16 pages, published in PAIR.

Office communication in U.S. Appl. No. 11/315,926, mailed Dec. 28, 2007, 17 pages, published in PAIR.

Amendment with Information Disclosure in U.S. Appl. No. 11/315,926, dated Mar. 28, 2008, 22 pages, published in PAIR.

Adams, M.L., Enzelberger, M., Quake, S., and Scherer, A., "Microfluidic integration on detector arrays for absorption and fluorescence micro-spectrometers,"Sensors and Actuators A, vol. 104, 2003, pp. 25-31.

European Search Report and Annex for Counterpart EPO Application No. EP 06 12 6522, dated Mar. 29, 2007, 2 pages.

Notice of Allowance and Fee(s) Due in U.S. Appl. No. 11/315,926, mailed Jul. 10, 2008, 11 pages, published in PAIR.

Office communication in U.S. Appl. No. 11/702,470, mailed Apr. 25, 2008, 22 pages.

Bernini, R., Campopiano, S., and Zeni, L., "Silicon Micromachined Hollow Optical Waveguides for Sensing Applications," IEE Jour. on Selected Topics in Quantum Electronics, vol. 8, No. 1, Jan./Feb. 2002, pp. 106-110.

Office communication in U.S. Appl. No. 10/922,870, mailed Jul. 26, 2007, 11 pages, published in PAIR.

Office communication in U.S. Appl. No. 10/922,870, mailed Sep. 24, 2007, 3 pages, published in PAIR.

Amendment in U.S. Appl. No. 10/922,870, dated Apr. 30, 2007, 15 pages, published in PAIR.

Amendment in U.S. Appl. No. 10/922,870, dated Sep. 14, 2007, 9 pages, published in PAIR.

Amendment in U.S. Appl. No. 10/922,870, dated Oct. 4, 2007, 9 pages, published in PAIR.

Notice of Allowance and Fee(s) Due and attached papers for U.S. Appl. No. 10/922,870, mailed Oct. 22, 2007, 7 pages, published in PAIR.

Notice of Allowance and Fee(s) Due and attached papers for U.S. Appl. No. 11/315,387, mailed Jun. 20, 2007, 23 pages, published in PAIR.

Notice of Allowance and Fee(s) Due and attached papers for U.S. Appl. No. 11/315,387, mailed Oct. 5, 2007, 7 pages, published in PAIR.

Amendment with Request for Continued Examination in U.S. Appl. No. 11/315,387, dated Sep. 18, 2007, 6 pages, published in PAIR.

Office communication in U.S. Appl. No. 11/316,660, mailed Mar. 8, 2007, 25 pages.

Amendment with Information Disclosure in U.S. Appl. No. 11/316,660, dated Jun. 6, 2007, 20 pages, published in PAIR.

Office communication in U.S. Appl. No. 11/316,660, mailed Oct. 19, 2007, 22 pages, published in PAIR.

Notice of Allowance and Fee(s) due and attached papers for U.S. Appl. No. 11/315,992, mailed Oct. 3, 2007, 19 pages, published in PAIR.

Communication from European Patent Office including extended European Search Report with European Search Report and Annex and European Search Opinion for counterpart EPO Application No. EPO 6126522, dated Apr. 5, 2007, 7 pages.

"Developing technology: HPLC-Chip/MS", Agilent Technologies, printed from www.chem.agilent.com on Aug. 2, 2005, 2 pages.

Singh, K., and Goddard, N.J., "Leaky ARROW Waveguides for Optical Chemical and Biosensors", (Abstract Submitted to Biosensors 1998).

Printed from dias.umist.ac.uk on Aug. 1, 2005, 2 pages.

"Abstracts of Published Work", printed from dias.umist.ac.uk on Aug. 1, 2005, 3 pages.

Goddard, N.J., Singh, K., Bounaira, F., Holmes, R.J., Baldock, S.J., Pickering, L.W., Fielden, P.R., and Snook, R.D., "Anti-Resonant Reflecting Optical Waveguides (ARROW), as Optimal Optical Detectors for MicroTAS Applications", printed from dias.umist.ac.uk on Aug. 1, 2005, pp. 1-5.

Sivaprakasam, V., Huston, A., Eversole, J., and Scotto, C., Multiple UV Wavelength Excitation and Fluorescence of Bioaerosols, 2nd Joint Conference on Point Detection, Williamsburg, VA, 2004, 10 pages.

Koch, M., Evans, A.G.R., and Brunnschweiler, A., "Design and fabrication of a micromachined Coulter counter", J. Micromech. Microeng. 9, 1999, pp. 159-161.

Notice of Allowance and Fee(s) Due in U.S. Appl. No. 12/098,584, mailed Oct. 6, 2008, 16 pages, published in PAIR.

Amendment in U.S. Appl. No. 11/702,470, submitted Jul. 25, 2008, 21 pages, published in PAIR.

Office communication in U.S. Appl. No. 11/702,470, mailed Oct. 31, 2008, 22 pages, published in PAIR.

Amendment in U.S. Appl. No. 11/702,470, submitted Jan. 30, 2009, 22 pages, published in PAIR.

Office communication in U.S. Appl. No. 11/702,470, mailed Mar. 13, 2009, 2 pages, published in PAIR.

Response to Interview Summary with Information Disclosure in U.S. Appl. No. 11/702,470, submitted Apr. 2, 2009, 5 pages, published in PAIR.

FIG. 2
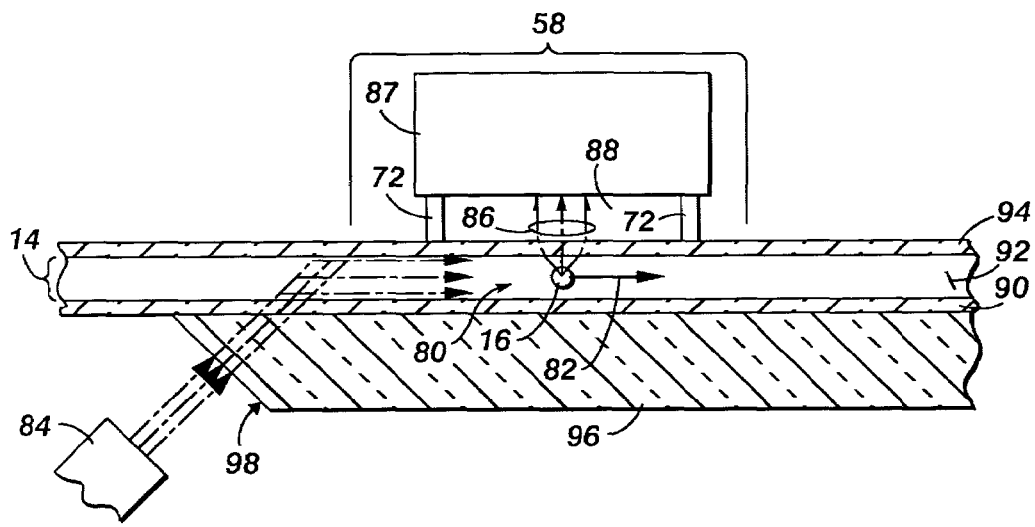
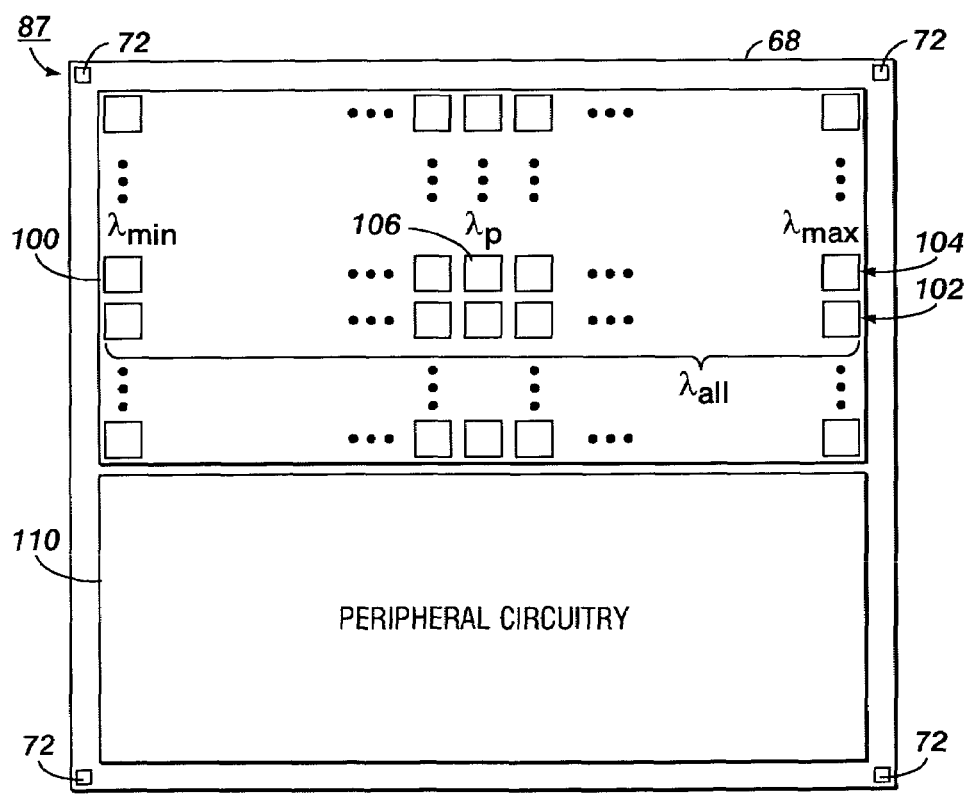
FIG. 3

FIG. 11
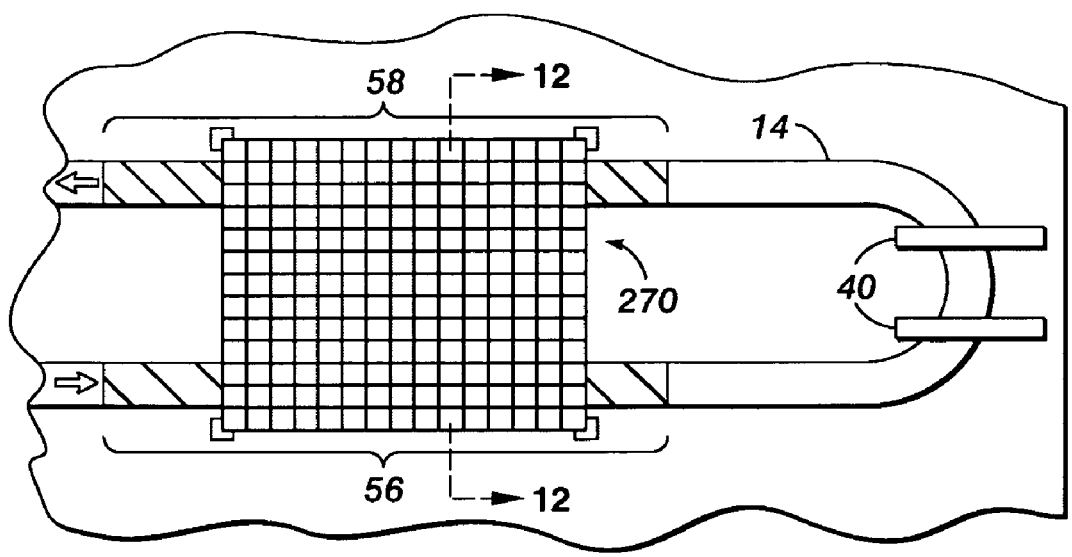
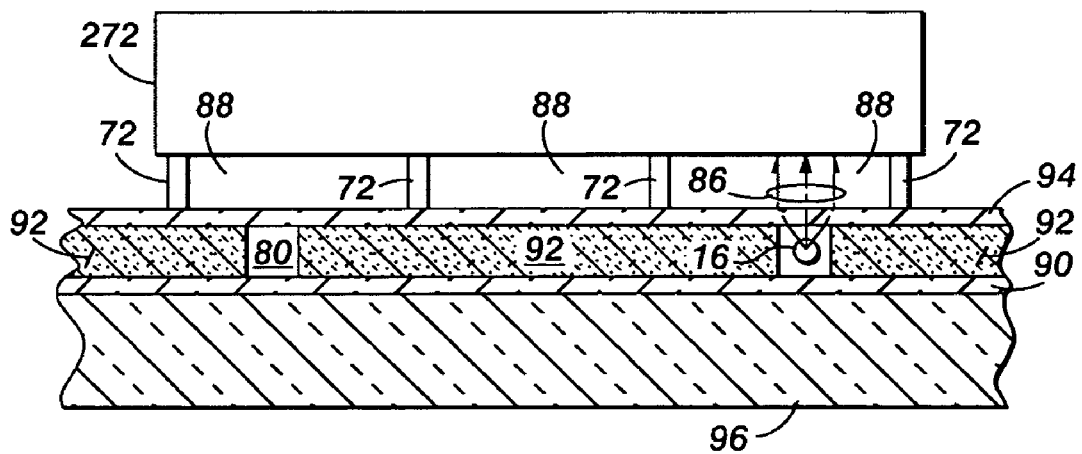
FIG. 12

FIG. 13
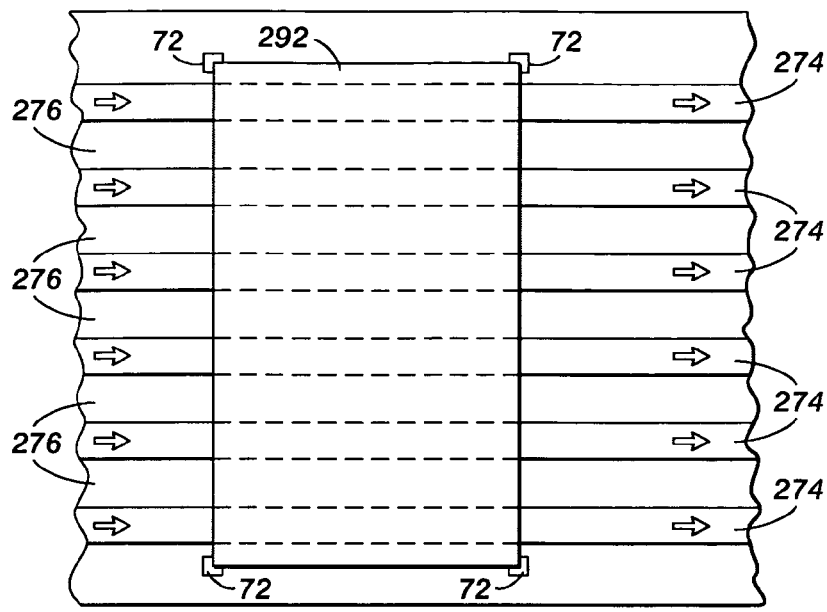
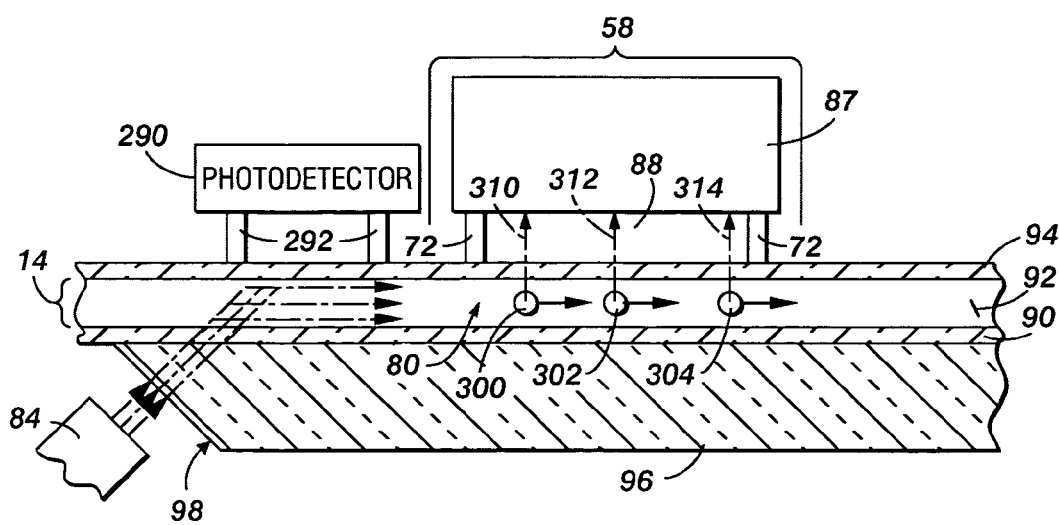
FIG. 14

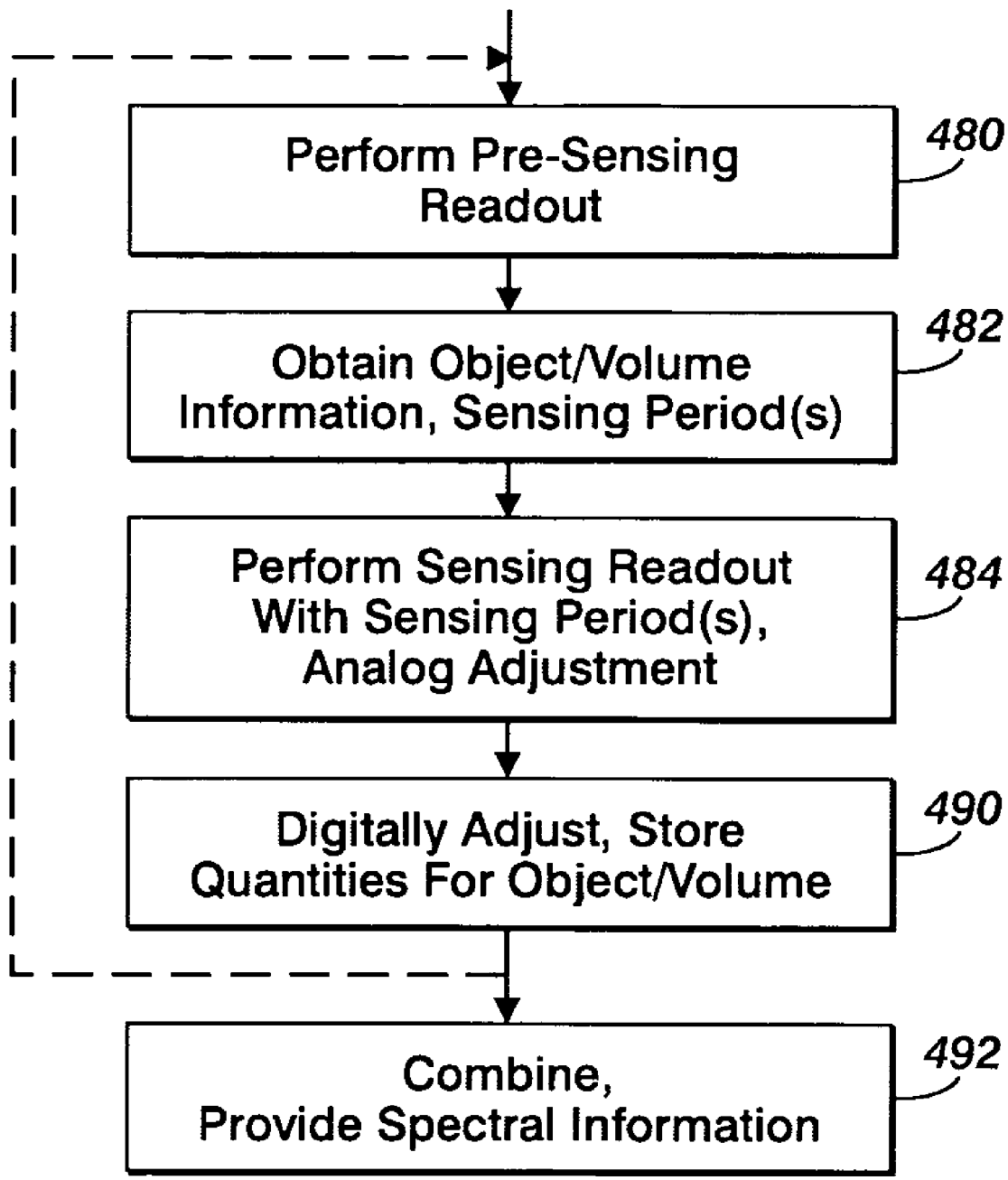

SENSING PHOTON ENERGIES EMANATING FROM CHANNELS OR MOVING OBJECTS

The present application is related to the following co-pending applications, each of which is hereby incorporated by reference in its entirety: "Chip-Size Wavelength Detector", U.S. patent application Ser. No. 10/922,870; "Anti-resonant Waveguide Sensors", U.S. patent application Ser. No. 10/976,434; "Bio-Enrichment Device to Enhance Sample Collection and Detection", U.S. patent application Ser. No. 11/007,121; "Photosensing Throughout Energy Range and in Subranges," Ser. No. 11/316,438; "Sensing Photon Energies of Optical Signals", U.S. patent application Ser. No. 11/315,926; "Sensing Photons from Objects in Channels", U.S. patent application Ser. No. 11/315,992; "Providing Light To Channels Or Portions", U.S. patent application Ser. No. 11/316,660; "Transmitting Light With Photon Energy Information", U.S. patent application Ser. No. 11/316,241; "Obtaining Analyte Information", U.S. patent application Ser. No. 11/316,303; "Propagating Light to be Sensed", U.S. patent application Ser. No. 11/315,387.

BACKGROUND OF THE INVENTION

The present invention relates generally to photosensing, and more particularly to photosensing with photosensor arrays on integrated circuits (ICs).

U.S. Pat. No. 5,166,755 describes a spectrometer apparatus in which a spectrum resolving sensor contains an opto-electronic monolithic array of photosensitive elements and a continuous variable optical filter. The filter can include a variable thickness coating formed into a wedge shape on a substrate or directly on the surface of the array. If polychromatic light, such as light reflected from a sample or a strip of a scene viewed from a spacecraft, passes through the variable filter and is spectrally resolved before incidence on the array, the output of all the elements in the array provides the spectral contents of the polychromatic light.

U.S. Pat. No. 6,580,507 describes a multiple-longitudinal flow cell channel system in which an array detector is positioned to monitor radiation from at least two of multiple flow cell channels, at separate groupings of pixels on the detector. Absorption or fluorescence of analytes in response to electromagnetic radiation can be monitored, where the analytes are contained in fluid flowing through the channels. Commonly available detector chips suitable for detecting visible wavelengths can be thinly coated with a lumagen or other fluorophore to facilitate UV sensitivity and mediate consistency of wavelength input to detector pixels.

It would be advantageous to have improved techniques for sensing light emanating from channels or moving objects.

SUMMARY OF THE INVENTION

The invention provides various exemplary embodiments, including methods, sensors, apparatus, and systems. In general, the embodiments are implemented with integrated circuits that include photosensor arrays.

These and other features and advantages of exemplary embodiments of the invention are described below with reference to the accompanying drawings.

BRIEF DESCRIPTION OF THE DRAWINGS

FIG. 2 is a schematic cross-sectional view of the analyzer in FIG. 1, taken along the line 2-2.

FIG. 3 is a schematic plan view of an implementation of an assembly that can be used in FIG. 2, including an integrated circuit (IC) with a photosensor array.

FIG. 11 is a schematic diagram of an alternative implementation of part of an analyzer on a fluidic structure as in FIG. 1.

FIG. 12 is a schematic cross-sectional view of the alternative implementation in FIG. 11, taken along the line 12-12.

FIG. 13 is a schematic plan view of a portion of an alternative implementation of an analyzer as in FIG. 1.

FIG. 14 is a schematic cross-sectional view of an alternative implementation of the sensing component in FIG. 2.

FIG. 18 is a flow chart showing general operations implementing the detect, readout, and combine routine of FIG. 17.

DETAILED DESCRIPTION

Figure 1:
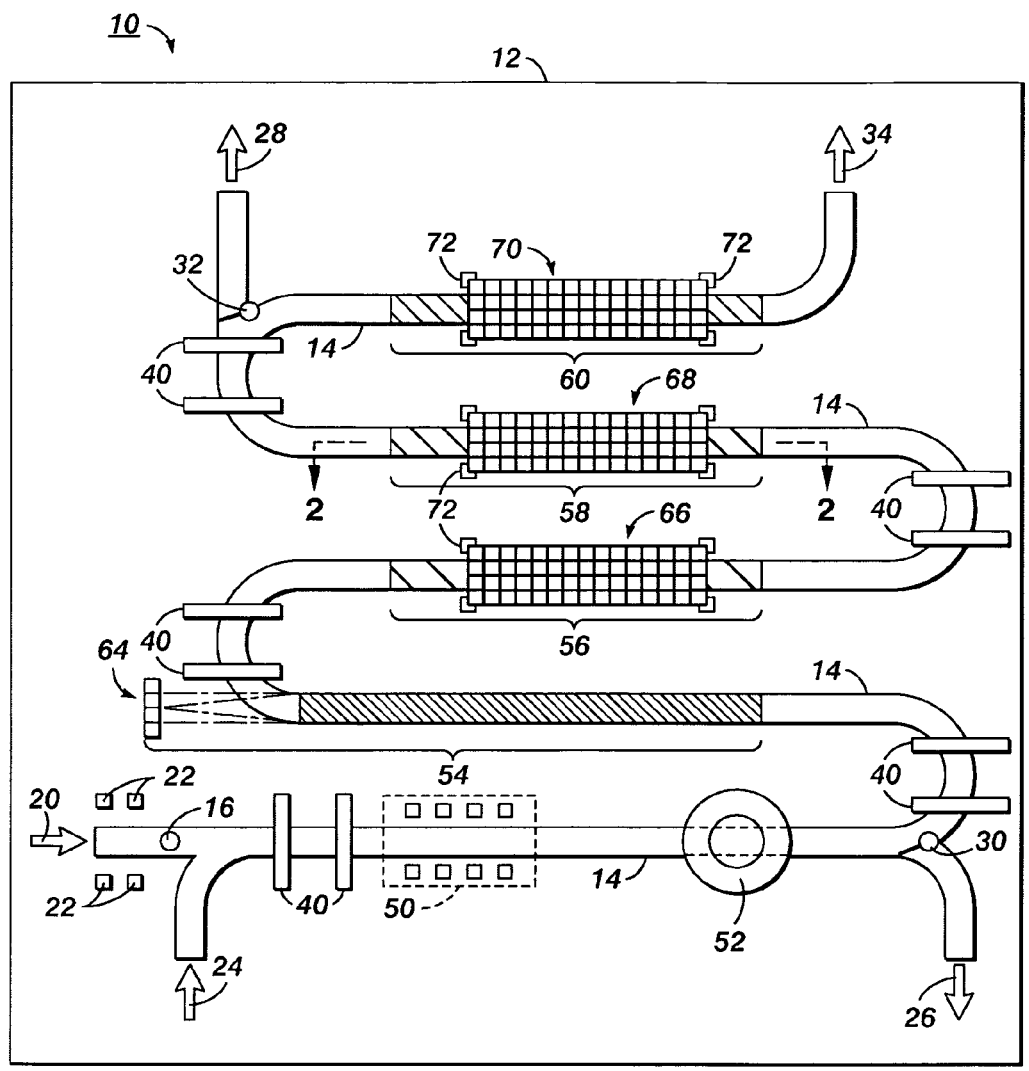
FIG. 1 is a schematic diagram of an analyzer on a fluidic structure.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum. The term "photon" refers herein to a quantum of light, and the term "photon energy" refers herein to the energy of a photon.

The various exemplary implementations described below address problems that arise in obtaining information about light. One of those problems is the difficulty of obtaining spectral information about light emanating from moving objects or from a channel in a fluidic structure rapidly and without bulky, expensive equipment. This is extremely important for optical characterization of moving objects that are hard to capture (or which it is not desired to capture) and that must be measured while moving. In addition, optical techniques for identifying particles obtain limited information and are constrained by weak interaction with excitation light.

The term "optical signal" is used herein to refer to a signal in the form of light. For example, an optical signal may "emanate from a point-like source", meaning that the light behaves as if its source were a point or had a very small area; for example, the light could be emitted or scattered by a particle or a compact group of particles.

The term "sensing" is used herein in the most generic sense of obtaining information from a physical stimulus; sensing therefore includes actions such as detecting, measuring, and so forth. A "sensor" is a component that performs some type of sensing, obtaining information from a physical stimulus. To "photosense" is to sense photons, and to "photosense quantity" of photons is to obtain information indicating a quantity of the photons. Photons that are photosensed are sometimes referred to herein as "incident photons".

A "photosensor" is used herein to refer generally to any element or combination of elements that senses photons, whether by photosensing quantity or any other information about the photons. A photosensor could, for example, provide an electrical signal or other signal that indicates sensed information, such as a signal indicating quantity of incident photons. If electrical sensing events occur in a photosensor in response to incident photons, the photosensor may integrate or otherwise accumulate the results of the electrical sensing events during a time period referred to herein as a "sensing period".

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width. A "subrange" of a range of photon energies is a part of the range, and can be similarly described. A "fluorescence subrange", for example, is a subrange in which fluorescence emissions occur, while a "scattering subrange" is a subrange in which light scattering occurs.

In general, each application of photosensing has a characteristic energy range, referred to as the "application's energy range", which is the range of photon energies over which it is necessary to obtain information in order that the application satisfies the relevant performance criteria. For example, if an application uses helium arc lamps, its energy range could encompass helium's major emission peaks.

In general, the upper and lower boundaries and widths of ranges and subranges are approximate. To photosense quantity of photons "throughout", "within", or "in" a range or subrange means to obtain information about quantity of photons that are predominantly within the range or subrange. In typical cases, between 60-90% of the sensed quantity of photons having energies within the range or subrange, but the percentage could be lower or higher. In some applications, 90% or even 95% or more of the sensed quantity of photons have energies within the range or subrange. Where an application requires that a minimum percentage or other proportion of sensed quantity of photons have energies within a range or subrange, the minimum percentage or other proportion is referred to herein as the "application's minimum photon proportion".

Some of the photosensing implementations described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In general, the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

An "integrated circuit" or "IC" is a structure with electrical components and connections produced by microfabrication or similar processes. An IC may, for example, be on or over a substrate on which it was produced or another suitable support structure. Other components could be on the same support structure with an IC, such as discrete components produced by other types of processes.

Implementations described herein include features characterized as "cells" and "arrays", terms that are used with related meanings: An "array" is an arrangement of "cells". An array on an IC or other support structure may also include circuitry that connects to electrical components within the cells such as to select cells or transfer signals to or from cells, and such circuitry is sometimes referred to herein as "array circuitry". In contrast, the term "peripheral circuitry" is used herein to refer to circuitry on the same support surface as an array and connected to its array circuitry but outside the array. The term "external circuitry" is more general, including not only peripheral circuitry but also any other circuitry that is outside a given cell or array.

Some of the implementations below are described in terms of "rows" and "columns", but these terms are interchangeable. Also, rows and columns are described herein as examples of "lines". Within an array, a "line" of cells refers herein to a series of cells through which a line can be drawn without crossing areas of cells that are not in the line. For example, in a two-dimensional array in which cells have uniform areas, a line of cells could be a row, a column, a diagonal, or another type of straight line; more generally, a line of cells could be straight or could include one or more non-straight features, such as curves or angles.

A "photosensor array" is an array in which some or all of the cells are or include photosensors. Accordingly, an IC "includes" a photosensor array if the IC includes an array of cells, and at least some of the cells include respective photosensors. A cell that includes a photosensor may also include "cell circuitry", such as circuitry that makes connections with the photosensor, that transfers signals to or from the photosensor, or that performs any other function other than photosensing. In general, a cell's photosensor and cell circuitry are within a bounded area of the array, an area sometimes referred to herein as the "cell's area". The part of a cell's area in which an incident photon can be photosensed is referred to herein as "sensing area".

In an application that includes a photosensor array, circuitry that "responds to" the photosensor array can be any circuitry that, in operation, receives information from the photosensor array about its photosensing results through an electrical connection. Circuitry that responds to a photosensor array could be circuitry in the photosensor array, or it could be peripheral circuitry or other external circuitry, or it could include any suitable combination of array circuitry, peripheral circuitry, and other external circuitry.

FIG. 1 shows schematically some components of analyzer 10 on support structure 12, a fluidic structure. Defined in support structure 12 is serpentine channel 14 through which an object 16 can travel, carried by a fluid or other appropriate substance. Object 16 can, for example, be a droplet or small volume of fluid that includes an analyte to be analyzed.

The term "object" is used herein in the general sense of any distinguishable thing from which light can emanate, whether through emission (e.g. radiation, fluorescence, incandescence, luminescence, etc.), scattering (e.g. reflection, deflection, diffraction, refraction, etc.), or transmission. The light "emanates from" or is simply "from" the object.

Examples of objects that could occur in implementations as described below include droplets, small volumes of fluid, single molecules, agglomerated molecules, molecule clusters, cells, viruses, bacteria, proteins, DNA, microparticles, nanoparticles, and emulsions. A droplet or small volume of fluid may, for example, include atoms, molecules, or other particles that emit light spontaneously or in response to excitation; a particle could be a "fluorescent component" of a droplet, fluorescing in response to excitation. Or a droplet may include particles that scatter light incident on the droplet in a way that depends on photon energy, so that the droplet scatters the incident light correspondingly; in this case, a particle could be a "scattering component" of a droplet. An analyte (i.e. a chemical species being investigated) in a droplet can act as a fluorescent or absorbent component.

An object "travels" or is caused "to travel" if the object moves through a succession of positions. For example, the object could be conveyed in a fluid, such as a liquid, gas, or aerosol, in which case the object may be referred to as being "carried" by the fluid.

Some exemplary implementations of the invention involve fluidic techniques for causing objects to travel along paths; as noted above, the term "fluid" is used herein to encompass liquids, gasses, and aerosols. The terms "fluidic structure" and "channel" are used herein with related meanings: A "fluidic structure" is a structure that depends for its operation on fluid positioning or fluid flow, such as, for liquids or gases, in response to pressure or, for liquids, as a result of surface tension effects; a "channel" is any tube or other enclosed passage defined within a fluidic structure and through which fluid flows during operation. A "channel portion" or simply "portion" refers to a part of a channel that can function as described.

An object "travels" within a channel or a portion of a channel or is caused "to travel" within a channel or a portion if the object moves through a succession of positions in the channel or portion. "One object at a time" is caused to travel through a portion of a channel if, from the relevant objects, only one is in the portion at a time. A "fluid propelling component" is a component that pumps or otherwise propels fluid within a channel. The direction in which fluid flows within a channel is sometimes referred to herein as a "flow direction". A series in which sets of cells are positioned "extends in" a flow direction if positions of consecutive sets in the series are displaced one from another in the flow direction, with one set's position being upstream from the other.

Object 16 enters channel 14 carried by a primary fluid illustrated by arrow 20, and can enter from a supply reservoir (not shown) and a sample well (not shown), with its entry into the primary fluid controlled by metering electrodes 22. The supply reservoir could, for example, be a microfabricated bio-enrichment device with a cell on which concentration occurs, as described in co-pending U.S. patent application Ser. No. 11/007,121, entitled "Bio-Enrichment Device to Enhance Sample Collection and Detection" and incorporated herein by reference in its entirety. Separated bands in the bio-enrichment sample well could be selectively directed into channel 14. Rather than electrical metering, as with electrodes 22, pressure metering could be used. Other possible techniques that could be implemented to provide a droplet or other small object to channel 14 could employ capillary forces or electro-osmotic flow pumps.

Although FIG. 1 illustratively shows an implementation with only one channel 14 receiving analyte samples from a single sample well (not shown) or other analyte container, analyzer 10 could be implemented with any appropriate number of channels similar to channel 14, and with each channel receiving analyte samples from a respective sample well. Furthermore, each of the channels could have a different combination of components suitable to a specific type of analysis such as fluorescence spectroscopy, laser-induced fluorescence spectroscopy (LIF), absorption spectroscopy, excitation spectroscopy, Raman scattering, surface-enhanced Raman scattering (SERS), far-infrared spectroscopy, etc. Each sample well could continuously collect a specific analyte for stationary or post-detection schemes. The channels could be formed by subdividing a broad channel into several parallel channels.

Additional fluid to carry object 16 may enter as shown by arrow 24, such as to permit a constant flow rate or consistent flow independent of the analyte supply. The path followed by the fluid in channel 14 can be controlled through a number of devices. For example, the fluid, together with object 16 if appropriately positioned, can be purged at two outlets as illustrated by arrows 26 and 28 through toggling of valves 30 and 32, respectively, each of which is at a bifurcation junction. Rather than valves, other types of gates could be used, such as electric fields to selectively deflect objects; charged particles could be deflected by Coulomb force, and polarizable particles could be deflected by dielectrophoretic force. If the fluid is not purged by operating valves 30 and 32 or other similar valves (not shown) or by some other type of gate, it is purged at a final outlet from channel 14, illustrated by arrow 34.

The flow of the fluid can be maintained by conventional propulsion components such as electro-osmotic pumps 40 or some suitable hydraulic pressure pump appropriately positioned along the length of channel 14. A wide variety of other propulsion components could be used, including, for example, gas pressure pumps, positive displacement pumps, micro-peristaltic pumps, electro-kinetic pumps, piezo pumps, and thermal mode pumps. Various techniques for fluid propulsion are described in Devasenathipathy, S., and Santiago, J. G., "Electrokinetic Flow Diagnostics", in Breuer, K. S., Ed., *Micro and Nano-Scale Diagnostic Techniques*, Springer-Verlag, New York, 2003, pp. 113-154, incorporated herein by reference. In addition to maintaining flow of fluid, propulsion components can also perform system flush and initial fluid loading functions, with pressure driven techniques. Appropriate circuitry (not shown) can coordinate the various pumps and other components to work in a synchronized manner.

Pressure driven flow creates a parabolic velocity profile due to fluid resistance at the walls of a channel, which leads to band spreading. Spreading and other forms of band distortion will also be evident in fluid passing through one of the serpentine curves in channel 14. Appropriate techniques can be used to track discrete analytes and provide flow cross-section commensurate with analyte size.

Electro-osmotic flow (EOF) results from motion of ions inside the Debye layer due to an applied electric field in a channel direction. A Debye layer forms if the channel walls charge up when in contact with the solvent, e.g. water. The charged wall surface attracts oppositely charged counter ions, which concentrate in a thin layer next to the surface. The Debye layer has a thickness of $$\lambda_D = \left(\frac{\varepsilon kT}{q^2 n}\right)^{1/2},$$

where $\varepsilon$ indicates the dielectric constant, k indicates the Boltzman constant, T indicates the temperature, q indicates the ion charge, and n indicates the concentration of ions. Application of a potential difference in the direction of the channel causes the Debye layer to move with the electric field and, due to viscous drag, to create bulk fluid flow. The velocity profile is flat so that band distortion is a minimum. It should be noted, however, that EOF is dependent on wall charge, which is in turn affected by pH.

Various techniques can be used to control the flow of analytes, such as by directing them into different channels depending on their properties. This allows purging of benign or uninteresting particles, or the use of different detection schemes for different classes of particles that have been identified in initial detection steps. For example, the propulsion components can be coordinated with appropriate additional components for gating, metering, sorting, bifurcating, and otherwise logically controlling flow, such as with valves 30 and 32 and other appropriate devices controlled by switching electrodes and charge control.

Along channel 14 is a series of sensing components, each of which obtains information about object 16 as it travels within a respective straight portion of channel 14; the straight portions are separated by 180-degree curved portions, allowing a compact arrangement of several sensing components and interactive detection. Coulter counter 50 and Mie scatter sensor 52, for example, are conventional sensing components, illustratively along parts of one straight portion of channel 14. Coulter counter 50 is an example of an electrically based particle size detector, and could be implemented as described, for example, in Koch, M., Evans, A. G. R., and Brunnschweiler, A., "Design and Fabrication of a Micromachined Coulter Counter", *J. Micromech. Microeng.*, Vol. 9, 1999, pp. 159-161, incorporated herein by reference. Mie scatter sensor 52 is an example of an optical detector that relies on particle-induced scattering of light entering from the side of channel 14.

Coulter counter 50 can be implemented to size particles in the 1-10 μm range within a continuous liquid stream. The Coulter counter technique should also work for other particle sizes as long as the inner diameter of channel 14 in the sensing region is not more than an order of magnitude larger than the particles being measured. Also, larger particles are harder to handle in microfluidic systems, i.e. fluidic systems in which channels have maximum transverse inner dimensions less than 0.1 mm; in such systems, larger particles tend to sediment if their density is greater than that of the solvent.

In Coulter counter 50, particles suspended in an electrically conducting solution can be drawn through a small aperture between two electrodes. A voltage applied across the aperture creates a sensing zone, and each particle passing through the sensing zone displaces its own volume of conducting liquid. The particle has infinite resistance, even if itself conductive, because polarization effects at the particle-electrolyte interface prevent any current from flowing through the particle itself. Therefore, the particle's resistance causes a momentary increase of impedance across the aperture. This change in impedance produces a tiny current flow that can be received by an amplifier and converted into a voltage pulse large enough for accurate measurement.

The Coulter principle states that the amplitude of this pulse is directly proportional to the volume of the particle, so that scaling pulse heights in volume units provides information about particle size. A size distribution can be obtained and displayed.

Mie scattering is another conventional technique for determining particle size in a free stream. Mie scattering refers to the elastic interaction of electromagnetic waves with particles having diameter at least one-tenth of the wavelength of incident light. The radiation pattern is predominantly forward scatter, with an invariant scattered angular pattern that is symmetrical along the axis of incident light for a perfect sphere. The scattered intensity increases with sphere radius, so that large particles may be distinguished from small particles by the strength of light reflected from their surfaces at a given angle. Mie scattering using light of different wavelengths has been successfully applied to size measurements of single bioaerosol particles.

The series of sensing components also includes optical (e.g. visible or infrared) absorption sensing component 54, first fluorescence sensing component 56, second fluorescence sensing component 58, and Raman scatter sensing component 60. These are merely exemplary, however, and analyzer 10 could include any other suitable combination of sensing components, including some that are not connected in series. In particular, additional sensing components (not shown) could include conventional optical or electrical trigger elements that provide a signal indicating when an analyte with properties meeting certain criteria moves past a position along channel 14. Furthermore, it may be possible to include sensing components for electrical impedance spectroscopy (EIS) for electronic pathology rather than sensing differential resistance for bioparticle sizing.

A signal indicates "spectral information" about photons if it indicates information about quantities of the photons with energies in each of a set of subranges of a range of photon energies. The spectral information could, for example, be a "spectral distribution" in which quantities in non-overlapping subranges are indicated. More specifically, a "complete spectral distribution" is a spectral distribution in which the subranges cover substantially all of an application's energy range.

A series of sensing components as in FIG. 1 makes it possible to obtain spectral information about moving particles or other objects in order to achieve orthogonal characterization and reliable identification. Characterization is orthogonal if sensing components obtain information about orthogonal characteristics of a moving object, such as by photosensing different ranges of photon energies; sensing components could also be suitable for different intensity ranges. By choosing suitable materials, it is possible to obtain spectral information for the entire range from the deep ultraviolet to the far infrared or even for frequencies in the THz range.

Analyzer 10 can be designed to perform multi-signal analysis for a specific application, whether high wavelength resolution or broadband detection is desired. The technique illustrated in FIG. 1 also takes advantage of the motion of object 16 with a geometry that enables long integration times without sacrificing throughput capacity. Highly sensitive optical characterization methods can be used, such as fluorescence spectroscopy (illustratively in more than one range of photon energies) and Raman spectroscopy. Sivaprakasam, V., Houston, A., Scotto, C., and Eversole, J., "Multiple UV Wavelength Excitation and Fluorescence of Bioaerosols", *Optics* Express, Vol. 12, No. 9 (2004), pp. 4457-4466, have shown that using different UV excitation ranges provides more specific information about an analyte. Also, the use of multi-signal analysis makes it possible to perform reagentless bioagent identification.

Each of sensing components 54, 56, 58, and 60 includes a respective one of ICs 64, 66, 68, and 70, features of which are described in greater detail below. In general, however, each of these ICs includes a photosensor array, and the sensing component includes a set of cells of the photosensor array. The set of cells photosenses photons within a range of photon energies; for example, the sets of cells in ICs 66 and 68 could photosense different ranges of photon energies in the visible to ultraviolet range, and, as noted above, the set of cells in IC 70 could photosense in the infrared. Furthermore, more than one IC, such as ICs 66 and 68, could photosense fluorescing photons that are in the same energy range, but that result from excitation at different wavelengths such as from different LED or laser light sources. As explained in greater detail below, the set of cells for each of sensing components 54, 56, 58 and 60 includes a subset of cells, each of which photosenses in a respective subrange, and the subranges of at least two of the cells are different from each other.

Subranges of photosensing are "different from each other" in a given application if, at the application's minimum photon proportion, the subranges produce distinguishable photosensing results when the application requires. For example, if two subranges are so similar that their photosensing results cannot be distinguished when required, they are not different from each other. It should be noted, however, that subranges that are different from each other can nonetheless overlap or one of them can include another.

As described in greater detail below, sensing components 56, 58, and 60 can each be implemented with any suitable excitation or illumination technique to cause emanation of light from objects. One such technique, for example, is enhanced light-target interaction, which can be accomplished by anti-resonant waveguide techniques or other suitable excitation techniques. Enhanced light-target interaction is especially important if analyzer 10 is characterizing single particles or low concentrations of biological or chemical agents. In general, an anti-resonant waveguide has a core region surrounded by a cladding layer with a higher refractive index than the core region. Where the core region is a fluid that contains an analyte, light can be guided within the fluid, permitting photonic interaction over an extended length of a channel such as channel 14. As illustrated in FIG. 1, ICs 66, 68, and 70 are therefore supported on spacers 72, providing a suitable gap between each IC and the respective portion of channel 14 to avoid interference with anti-resonant waveguiding.

Anti-resonant waveguide techniques are described in greater detail in co-pending U.S. patent application Ser. No. 10/976,434, entitled "Anti-resonant Waveguide Sensors" and incorporated herein by reference in its entirety. Additional techniques are described in Goddard, N. J., Singh, K., Bounaira, F., Holmes, R. J., Baldock, S. J., Pickering, L. W., Fielden, P. R., and Snook, R. D., "Anti-Resonant Reflecting Optical Waveguides (ARROWs) as Optimal Optical Detectors for MicroTAS Applications", dias.umist.ac.uk/NJG/Abstracts/MicroTAS/MicroTas2. htm, pp. 1-5, and Singh, K., and Goddard, N. J., "Leaky Arrow Waveguides for Optical Chemical and Biosensors", (Abstract Submitted to Biosensors 1998), dias.umist.ac.uk/NJG/Abstracts/Biosensors/ARROW-Biosensors.htm, pp. 1-2, both of which are incorporated herein by reference.

In optical biosensors, the interaction between light and target molecules is typically very weak. Techniques in which light propagates in a longitudinal direction, such as anti-resonant waveguide techniques, can improve the interaction because of the extended length in which interaction occurs. Also, such techniques are very suitable for multi-signal analysis because they are relatively unaffected by changes in wavelength or film thickness. More particularly, in contrast to excitation techniques that use evanescent fields of ordinary waveguides and therefore require very small channels, fluidic channels with maximum transverse dimensions as great as a few millimeters can be used as anti-resonant waveguides. Suitable configurations can include, for example, an aerosol in a glass capillary tube or a liquid film between glass slides. The excitation could be with visible light, ultraviolet light, infrared light, radiation in the terahertz range, or any other appropriate electromagnetic radiation. Examples of specific sensing components employing anti-resonant waveguide techniques are described in greater detail below.

The use of anti-resonant waveguides and other techniques for enhanced light-target interaction may require additional mechanisms to suppress background excitation light. The use of an anti-resonant waveguide, by itself, strongly reduces background detected by a photosensor array located parallel to the waveguide, as illustrated below. In addition, if each cell of a photosensor array is only photosensing a subrange of photon energies, additional background suppression occurs because other photon energies will not be photosensed; in some implementations, for example, they may be reflected from a coating over the photosensor array. Additional background suppression can be obtained using a wavelength filtering component as part of the wall of channel 14 or as an additional coating on top of a photosensor array.

FIG. 2 shows schematically a cross-section of analyzer 10 taken along the line 2-2 in FIG. 1. Although FIG. 2 therefore shows features of second fluorescence component 58, similar features would be found in first fluorescence sensing component 56 and, to an extent, in Raman scatter sensing component 60.

As object 16 travels through portion 80 of channel 14 in the downstream direction indicated by arrow 82, it receives light from an excitation component, illustratively light source 84 which could be a laser or an LED, for example; in general, excitation radiation in any of various different energy ranges can be coupled into channel 14 to produce anti-resonant waveguiding. Portion 80 can function as an anti-resonant waveguide in response to light from source 84, or it can function in another way that provides enhanced light-target interaction. For example, other techniques that provide continuous excitation to a fluorescing molecule include tracking the molecule in motion with a scanning laser beam; using a linear array of LEDs to sustain particle excitation along its path; arranging a collimated beam along the particle path without waveguiding; and providing a Fabry-Perot-style cavity in which light passes through the medium containing the particle several times.

Sensing components using anti-resonant waveguide modes are especially advantageous in combination with fluidic devices because the fluidic channels themselves can be used as anti-resonant waveguides in various configurations. Examples of configurations include an aerosol carrying analytes in a capillary, a liquid film carrying analytes within a channel or between glass slides, etc.

In response to light from source 84, an analyte within object 16 fluoresces, emitting light with a characteristic spectrum of photon energies. A portion 86 of the light is emitted toward assembly 87, which includes at least IC 68 and possibly also other structures. Photons in portion 86 can therefore be photosensed by cells of a photosensor array on IC 68. Assembly 87 is positioned so that the photosensor array on IC 68 is close to and parallel to the path of object 16 through portion 80, to increase light collection efficiency.

The term "path" is used herein to refer to a substantially continuous series of positions from which light may emanate (i.e. an "emanation path") or at which light is incident on a photosensor array (i.e. a "photosensing path"). A part of a path is referred to herein as a "segment", and segments may overlap or be included one in another.

A photosensor array is "positioned along" or "along" a path or a segment if the array is positioned near the path or segment in such a way that one or more of its photosensors can photosense light emanating from the path or segment.

Similarly, a photosensor array is "positioned along" or "along" a channel or a portion of a channel if the array is positioned near the channel or portion in such a way that one or more of its photosensors can photosense light emanating from the channel or portion.

An optical signal "follows" a photosensing path across an array if the optical signal, due to relative movement with the array, is successively incident on a series of positions within the path. An optical signal emanating from a point-like source can, for example, follow a "line-like path" across an array, meaning a photosensing path that approximates a line of cells.

Although segments of a photosensing path may overlap, segments are "distinct" if they do not overlap. Similarly, the sets of cells that photosense an optical signal in two segments of a path are "distinct" if they have no "shared cells", meaning cells that are in both sets.

An object "travels" or is caused "to travel" along a path if the object moves through a succession of positions in the path. For example, the object could be conveyed in a fluid, e.g. liquid, gas, or aerosol. "One object at a time" is caused to travel through a segment of a path if, from the relevant objects, only one is in the segment at a time. An "object movement component" is a component that causes one or more objects to travel along a path; for example, a fluid propulsion component can be an object movement component if the fluid being propelled contains objects.

Assembly 87 is illustratively supported on spacers 72 to avoid disturbing anti-resonant waveguiding in portion 80 of channel 14. Spacers 72 are positioned outside portion 80, and, as a result, air gap 88 below assembly 87 prevents disturbance of waveguiding because air has a lower refractive index than that of the liquid within the waveguide. Any other appropriate structure could be provided that would prevent disturbance of waveguiding; examples include a gas or vacuum layer or possibly even a liquid layer or film with a low refractive index. A thin gap, layer, or film that is only a few microns thick, e.g. 10 μm, is sufficient to prevent disturbance of waveguiding if it has a sufficiently low refractive index.

Because object 16 receives excitation continuously throughout portion 80, fluorescence also occurs continuously along the photosensor array. As a result, spectral information is collected continuously as object 16 moves through portion 80. As described below, a similar technique can be used for light scattered by object 16.

The structure shown in FIG. 2 could also be used to implement Raman scatter sensing component 60 in a way that, although not comparable to dedicated Raman sensors, may provide acceptable performance and resolution with sufficient spectral range for a given application such as for specific Raman bands of interest. The output signal could indicate a set of intensity ratios of selected Raman lines and/or certain narrow intervals of a Raman spectrum rather than a complete Raman spectrum. By focusing on key differentiators in a Raman spectrum, this technique could provide the most relevant input for data analysis and comparison against a library of Raman profiles or another such database. This approach may be more tractable and efficient as a first step than comparing an entire Raman spectrum with a huge library of profiles.

To implement a Raman scatter sensing component as shown in FIG. 2, it would be necessary that light source 84 and IC 68 meet appropriate specifications, especially with regard to sensitivity and background light suppression within analyzer 10. In addition, suitable optical elements would be necessary between channel 14 and the photosensor array of IC 68 to ensure efficient and suitable light sampling.

Exemplary differences between a fluorescence sensing component and a Raman scatter sensing component would be as follows: A fluorescence sensing component could include a photosensor array in which cells photosense within a wide spectral range with rather low resolution, e.g. 400-700 nm with a moderate wavelength resolution of 2-5 nm. In contrast, a Raman scatter sensing component could include a photosensor array in which cells photosense within a smaller spectral range close to the excitation wavelength but with greater resolution, e.g. 800-830 nm with a resolution of 0.2-0.5 nm or even higher resolution. The sensing range for Raman scatter sensing must be set in accordance with typical energies of Raman scattered photons, which are 100 cm$^{-1}$ to a few 1000 cm$^{-1}$ wavenumbers different from the excitation photon energy, where wavenumber $k=2\pi/\lambda$ in units of 1/cm.

FIG. 2 also illustrates one of the ways in which support structure 12 could be implemented. Support layer 90 could, for example, be a light-transmissive glass or silicon substrate. Channel 14 can be defined in a micromolded layer 92 of polydimethylsiloxane (PDMS). PDMS is an inexpensive, biocompatible, transparent, silicon based elastomer with controllable hardness, hydrophobicity, excellent gas permeability, and surface chemistries that can be tuned to specific applications. It is sufficiently transparent in the visible portion of the spectrum to allow visualization of fluidic transport and measurements through a portion of layer 92, such as by a photosensor array on IC 68. In patterning layer 92 and other layers in FIG. 2, the length of channel 14 in which light-target interaction occurs can be chosen to minimize interference between different analytes.

Techniques for producing a patterned layer of PDMS are described, for example, in Becker, H., and Gartner, C., *Electrophoresis*, Vol. 21, 2000, p. 12, incorporated herein by reference. For example, a template can be fabricated on glass from SU-8 polymer, and PDMS can then be deposited to form a patterned structure within the template. The template can then be removed. Over layer 92 is plate 94, such as glass and therefore another example of a light-transmissive structure.

The use of a patterned layer of PDMS is merely illustrative. A wide variety of other techniques could be used to produce microchannels or other channels suitable for analyzer 10. For example, techniques could be used that etch glass to produce channels. Also, channels could be microfabricated by patterning a layer of a polymer material such as SU-8 to produce high aspect ratio channel walls. Depending on the medium that carries analyte through channel 14, parameters of channel 14 can be modified for optimal results. If the medium is an ordinary fluid, for example, the optimal width of the channel will be different than if the medium is an aerosol. It may also be necessary to adjust the width of the channel to obtain a desired throughput.

Other dimensions of the structure shown in FIG. 2 can be changed to obtain desired results. For instance, the thicknesses of layers 90 and 94 can bear a desired relationship to the height of channel 14, depending on various constraints, including stability requirements, manufacturing convenience, and, as noted below, the need to accommodate a desired flow of fluid and objects through channel 14. Thicknesses of layers 90 and 94 are often greater than or approximately equal to the height of channel 14. Typical thicknesses range between approximately 100 μm and 2 mm. Channel height ranges from approximately 1 μm or less up to a few mm.

A specific parameter of channel 14 that can have significant effects is adhesiveness of the channel wall. For example, experiments with *B. Thurengiensis* on uncoated surfaces have shown that adhesion may be a concern. This would be especially important for microfluidic channels, i.e. channels with maximum transverse inner dimensions less than 0.1 mm—their characteristically high surface area to volume ratio could lead to significant system loss. Bioadhesion could also compromise the ability to track the passage of a sample analyte through the entire length of channel 14. Bioparticles are attracted to charged or highly polarized surfaces such as glass, plexiglass acrylic, silicon, and even polymeric materials. With prolonged contact, bacteria and proteins may adhere to almost any surface by exposing more of their hydrophobic core regions, thus adapting their contact area to the specific surface properties. Once such a molecule is sufficiently close (e.g. 1-10 nm) to any surface, van der Waal's force dominates, and adhesion becomes a significant issue.

Various techniques can be used to reduce sample loss through surface adhesion, such as by providing barriers that prevent bioparticles from coming too close to the surfaces. More specifically, an anti-adhesive coating can be applied to prevent bioparticles and other analytes from sticking to the walls. Dip-coated polyethylene glycol (PEG) is a good choice for preventing adhesion of most biomaterials such as bacteria and proteins. In addition, PEG may be very well suited for microfluidic devices, since PEG can maintain capillary force on aqueous solutions. Other coatings may be viable options depending on sample properties, material interface chemistry, and operating conditions and regimes; for example, parylene C or vapor deposited tetraglyme might provide appropriate coatings. As noted above, anti-resonant waveguiding techniques can employ a channel with an inner diameter at least up to approximately 1.0 mm and possibly greater, in which case adhesion is not as great a problem and clogging is unlikely to occur; nevertheless, anti-adhesion measures may be advantageous to prevent spurious background signals emitted by material adhering to a channel's inner wall.

FIG. 2 also shows optical component 96 on the side of support layer 90 opposite PDMS layer 92. Optical component 96 provides an appropriate surface 98 through which light from source 84 can be coupled into the anti-resonant waveguide within portion 80 of channel 14. Although shown as separate layers in FIG. 2, support layer 90 and optical component 96 could instead be fabricated from a single layer of material by suitable processes.

FIG. 3 is a schematic view of an implementation of assembly 87 in which IC 68 includes photosensor array 100 and also has spacers 72 attached to it, such as after microfabrication of array 100 and other components. Photosensor array 100 is illustratively a two-dimensional array, with at least two rows of cells that include photosensors.

Different rows or other parts of photosensor array 100 can be provided with different coatings or can be otherwise structured so that their cells photosense different ranges or subranges of photon energies. As a result, the information obtained from a single IC can provide a detailed analysis of incident photons over a broad range of photon energies. In addition, reference cells, such as the cells in row 102, can be used to provide a spatially resolved real-time reference signal, such as to continuously monitor position of an object emanating light as it moves past array 100.

Within an array, a "pair" of cells is any two cells; unless otherwise specified, the cells in a pair need not have any other specific relationship to each other. The cells in a pair are "near each other" if the distance between them meets a suitable criterion for nearness, such as being no greater than ten times the maximum diameter of the larger of the cells. In general, for example, two cells that are adjacent are also near each other. More generally, a set of cells are all "nearby" another cell if each cell in the set and the other cell, taken as a pair, are near each other. A feature of array 100 is that it includes one or more reference cells that are nearby to a subrange cell, such as by being adjacent to the subrange cell.

Each cell in row 102 photosenses photons throughout a suitable range, characterized as $\lambda_{all}$, to produce a reference for a nearby cell in row 104. For implementations in which it is advantageous to have signal strengths of the same order from a cell in row 102 and its paired cell in row 104, the cell in row 102 must be different from the cells in row 104. For example, it could have a different sensing area or it could have a gray filter coating different than a coating over the paired cell in row 104.

Each cell in row 104, on the other hand, photosenses a respective subrange between $\lambda_{min}$ and $\lambda_{max}$, with illustrative cell 106 photosensing a subrange centered around $\lambda_p$. IC 68 also includes array circuitry (not shown) as well as peripheral circuitry 110 which perform various functions relating to readout of photosensed information from array 100.

One advantage of the technique illustrated in FIG. 3 is that IC 68 provides a compact photosensor array that can be used for various functions within a system such as analyzer 10. The compactness of IC 68 also allows for an interactive detection scheme. Subsequent or adjacent ICs within analyzer 10 may exchange information or trigger events. The combination of analysis results from several ICs within analyzer 10 may help to obtain orthogonal information and ultimately enable reliable identification of object 16.

FIG. 4 illustrates another implementation of assembly 87, showing in greater detail how cells of an array photosense subranges, such as in row 104 in FIG. 3. As in FIG. 2, assembly 87 as in FIG. 4 can be supported over air gap 88 by spacers 72.

In FIG. 4, a cross-section has been taken through a fragment 150 of a photosensor array, with cells 152 of the fragment 150 shown schematically in cross-section. Over cells 152 is a transmission structure 160 that receives incident light 162, such as from an optional Selfoc® or other gradient index (GRIN) lens array, illustrated by lens array portion 164. Lens array portion 164 can be designed to receive light from air gap 88 as in FIG. 2 and to provide a parallel beam to structure 160, increasing spectral resolution.

A structure that "transmits" photons, sometimes referred to herein as a "transmission structure", is any material structure through which light can propagate. It is not necessary that there be a one-to-one relationship between photons that enter a transmission structure and photons that exit from it as long as the structure provides exiting photons in response to entering photons as a result of light propagation through the structure.

More generally, to "transmit" photons is to perform a function by which exiting photons at an exit position are provided in response to entering photons at an entry position as a result of light propagation between the entry and exit positions. To "transmit only" a specified set of photons from a first position to a second refers to a function that transmits photons from the first position to the second, but predominantly photons in the specified set. As with photosensing, described above, if a transmission structure transmits only a specified set of photons, between 60-90% of the transmitted photons are in the specified set, but the percentage could be lower or higher. In some applications, 90% or even 95% or more of the photons are in the specified set.

One type of transmission structure is a "coating", meaning a layered structure of light-transmissive material that is on or over another component such as a photosensor array. A coating varies "continuously" along a channel or path if the coating varies as a continuous function of its position along the path.

A transmission structure provides (and a cell receives from a transmission structure) photons "throughout", "within", or "in" a range or subrange if the provided photons are predominantly within the range or subrange. As with photosensing, described above, between 60-90% of the photons from a transmission structure typically have energies within the range or subrange, but the percentage could be lower or higher. In some applications, 90% or even 95% or more of the photons have energies within the range or subrange.

Transmission structure 160 can, for example, be a film with laterally varying light transmission properties as described, for example, in co-pending U.S. patent application Ser. No. 10/922,870, entitled "Chip-size Wavelength Detector", and incorporated herein by reference in its entirety. In the portion of transmission structure 160 shown in FIG. 4, wedge-shaped transmissive cavity 170 is enclosed between reflective films 172 and 174, forming a wedge-shaped Fabry-Perot etalon. Because its thickness varies as a function of position along the x-axis, transmission structure 160 will transmit different wavelengths as a function of position along the x-axis.

Figure 4:
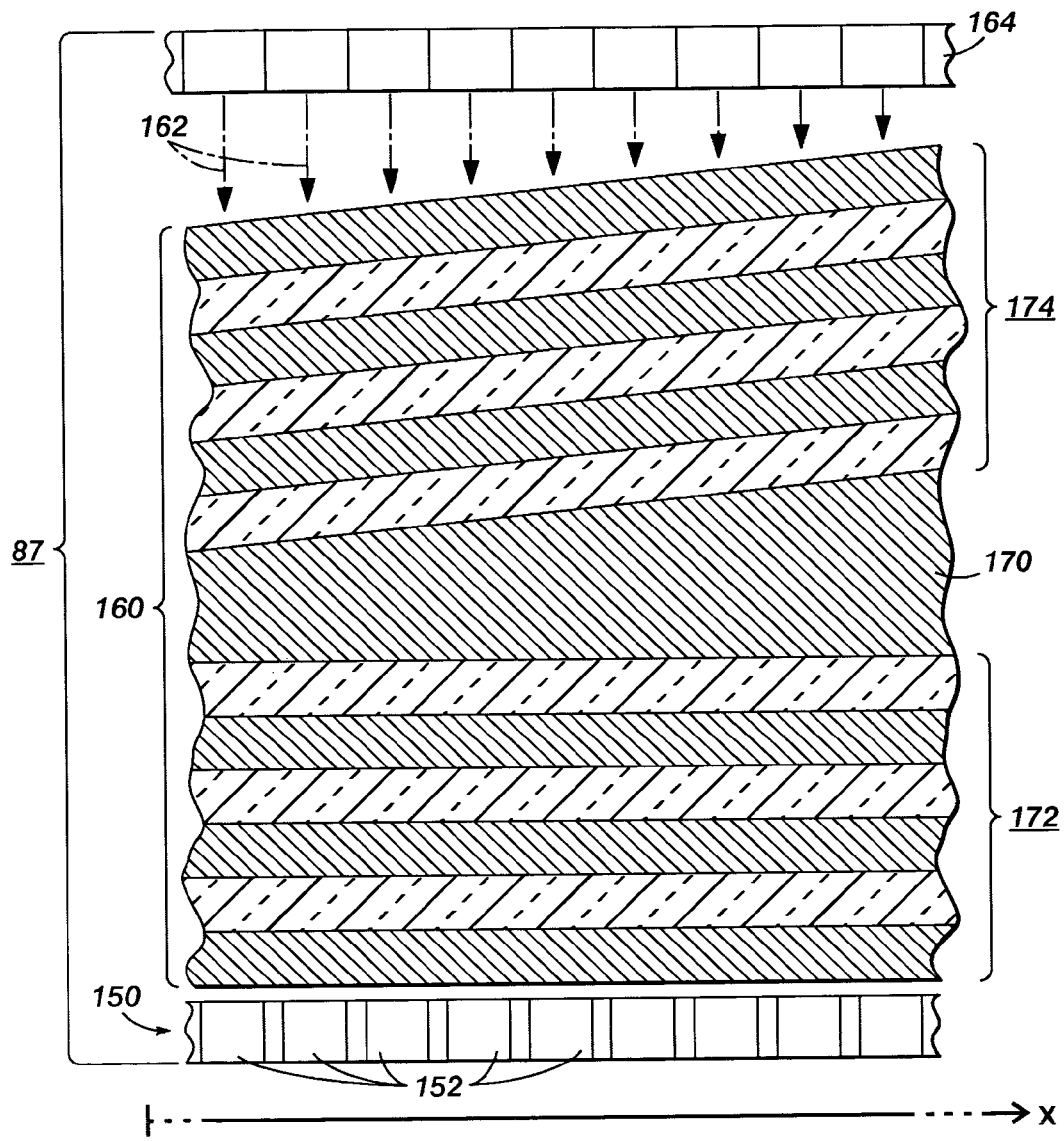
FIG. 4 is a schematic cross-sectional view of another implementation of an assembly that can be used in FIG. 2.

Transmission structure 160 can be produced with appropriate coatings on or over a photosensor array. Films 172 and 174 and cavity 170 could all be produced, for example, by exposure to deposition beams in an evaporation chamber; films 172 and 174 with uniform thicknesses could be produced by appropriate on-axis deposition, while cavity 170 with laterally varying thickness can be produced by appropriate off-axis deposition. FIG. 4 illustratively shows films 172 and 174 as relatively thick compared to cavity 170, which would be appropriate for layers of non-metallic material such as $SiO_2$, $TiO_2$, or $Ta_2O_5$, with thicknesses designed as described below; such materials are typically used to produce Bragg mirrors by depositing thin alternating layers with low absorption coefficients and large differences in refractive indices. If films 172 and 174 are reflective metal, however, they could be much thinner.

For an implementation with non-metallic material, specific thicknesses of cavity 170 and films 172 and 174 could be designed from the desired transmitted wavelength λ and the refractive index n of cavity 170. The thickness of cavity 170 is typically chosen to be $\lambda/(2n)$ or an integer multiple thereof, while the thicknesses of Bragg mirror layers within films 172 and 174 are typically $\lambda/(4n)$. The number of pairs of such layers in each of films 172 and 174 can vary between a few (e.g. 2-5) all the way up to 20 or 30, depending on the difference in refractive index between the two materials used, the desired transmission band width, and the desired stop band reflectivity. Therefore, in typical implementations, films 172 and 174 are much thicker than cavity 170, as suggested in FIG. 4.

Figure 5:
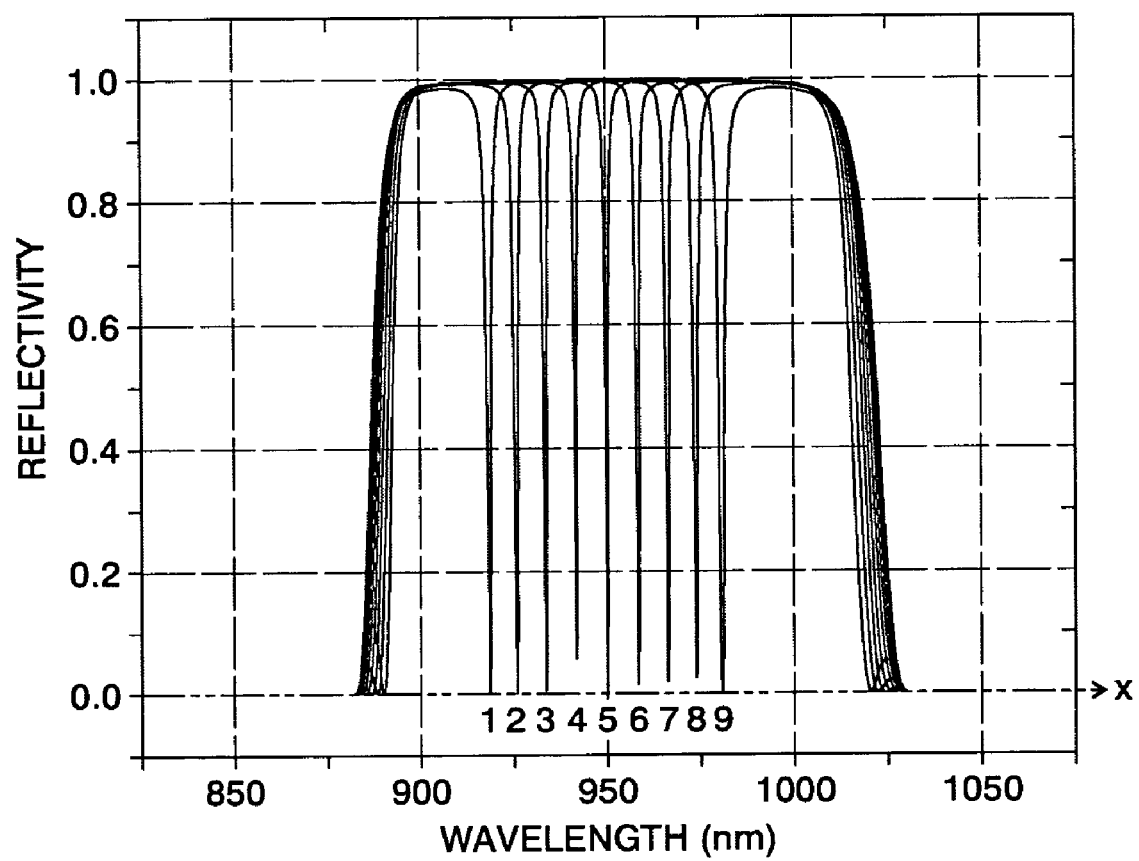
FIG. 5 is a graph illustrating laterally varying light transmission properties of a transmission structure in FIG. 4.

FIG. 5 illustrates the laterally varying light transmission properties of transmission structure 160. Because its thickness varies as a function of position along the x-axis, cavity 170 transmits different wavelengths as a function of position along the x-axis. Wavelengths of photons predominantly transmitted to nine of cells 152 as in fragment 150 are illustrated by the low reflectivity minima labeled 1 through 9. As can be seen, the high-transmissivity photon energy range for transmission structure 160 varies laterally.

Figure 6:
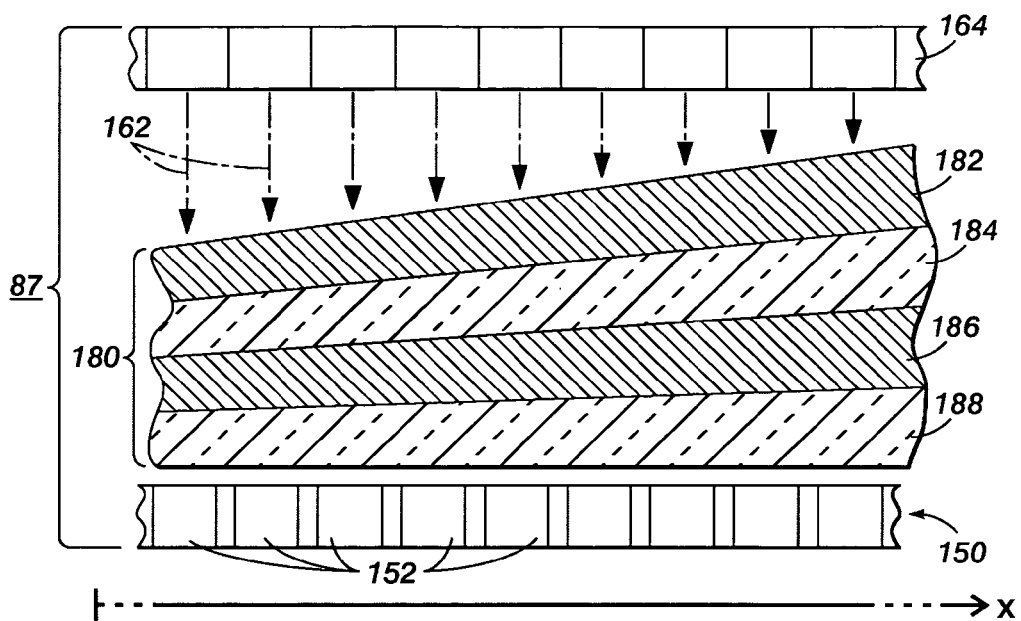
FIG. 6 is a schematic cross-sectional view of another implementation of an assembly that can be used in FIG. 2.

FIG. 6 illustrates another implementation of assembly 87, with features that have the same reference numbers as in FIG. 4 being implemented as described above. Rather than transmission structure 160, however, assembly 87 includes transmission structure 180. Transmission structure 180 can, for example, be a laterally graded Bragg mirror in which each of layers 182, 184, 186, and 188 is laterally graded. Each of layers 182, 184, 186, and 188 could be produced as described above for cavity 170, using off-axis deposition in an evaporation chamber.

Figure 7:
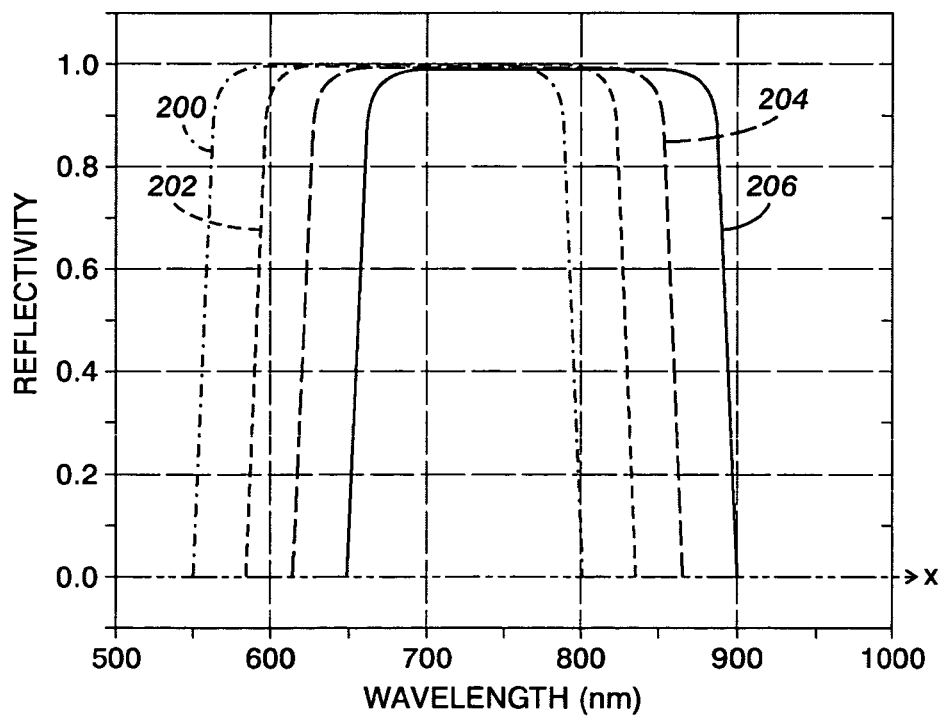
FIG. 7 is a graph illustrating the laterally varying light transmission properties of a transmission structure in FIG. 6.

FIG. 7 illustrates the laterally varying light transmission properties of transmission structure 180. Because its thickness varies as a function of position along the x-axis, transmission structure 180 reflects different wavelengths as a function of position along the x-axis. Curves 200, 202, 204, and 206 are shown, representing reflectivity of the portion of transmission structure 180 over each of four cells 152 in fragment 150, with curve 200 being for the leftmost cell of the four in FIG. 6 and curve 206 being for the rightmost cell of the four. As can be seen, the high-reflectivity photon energy range for transmission structure 180 varies laterally.

Figure 8:
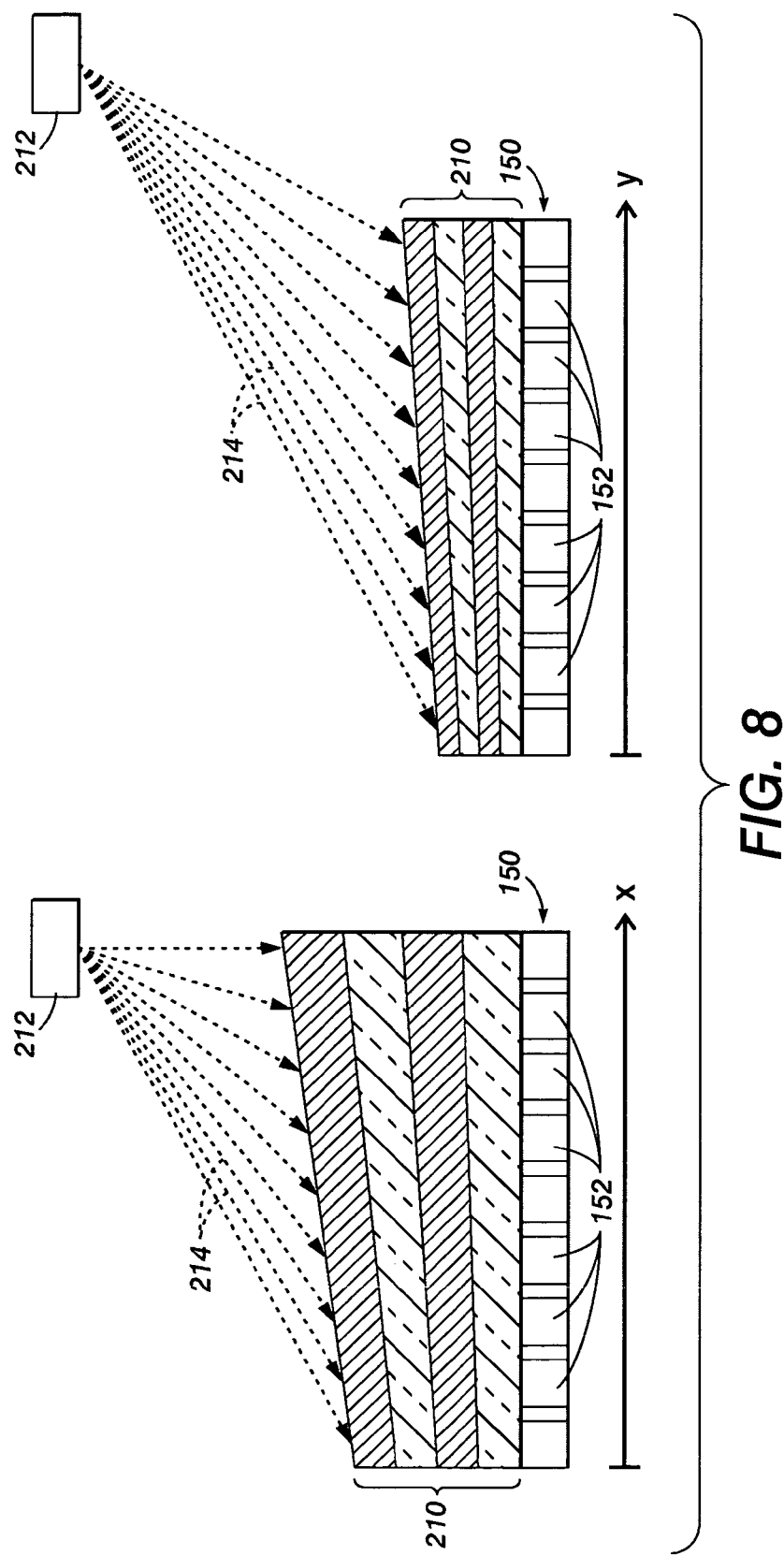
FIG. 8 illustrates a technique that produces a transmission structure that can be used in an assembly as in FIG. 2, showing orthogonal schematic cross-section views of deposition.

FIG. 8 illustrates a technique that produces transmission structure 210 with laterally varying light transmission properties similar to those illustrated in FIGS. 5 and 7 but with lateral variation in each of two dimensions. This technique can be used to produce different coatings for different rows of a photosensor array so that their cells photosense different ranges or subranges of photon energies, and can be used separately or in combination with reference cells.

Transmission structure 210 is produced on or over cells 152 of photosensor array 150 by using deposition source 212 to provide deposition beam 214 that can be characterized at any given point on the surface of structure 210 by two angles. One of the two angles results from angular variation of deposition beam 214 in the x-direction across array 150, while the other results from angular variation in the y-direction. As a result, the thickness gradient of structure 210 is similarly different in the x- and y-directions. Therefore, cells within each row extending in one of the two directions will photosense a range of photon energies similarly to FIG. 7, but the range will be different than the range photosensed by cells in any other row extending in the same direction.

The technique of FIG. 8 could be implemented in a variety of ways. For example, during deposition, structure 210 could be formed on a support structure that is tilted as required, deposition source 212 could be tilted as required, or both kinds of tilt could be employed.

Figure 9:
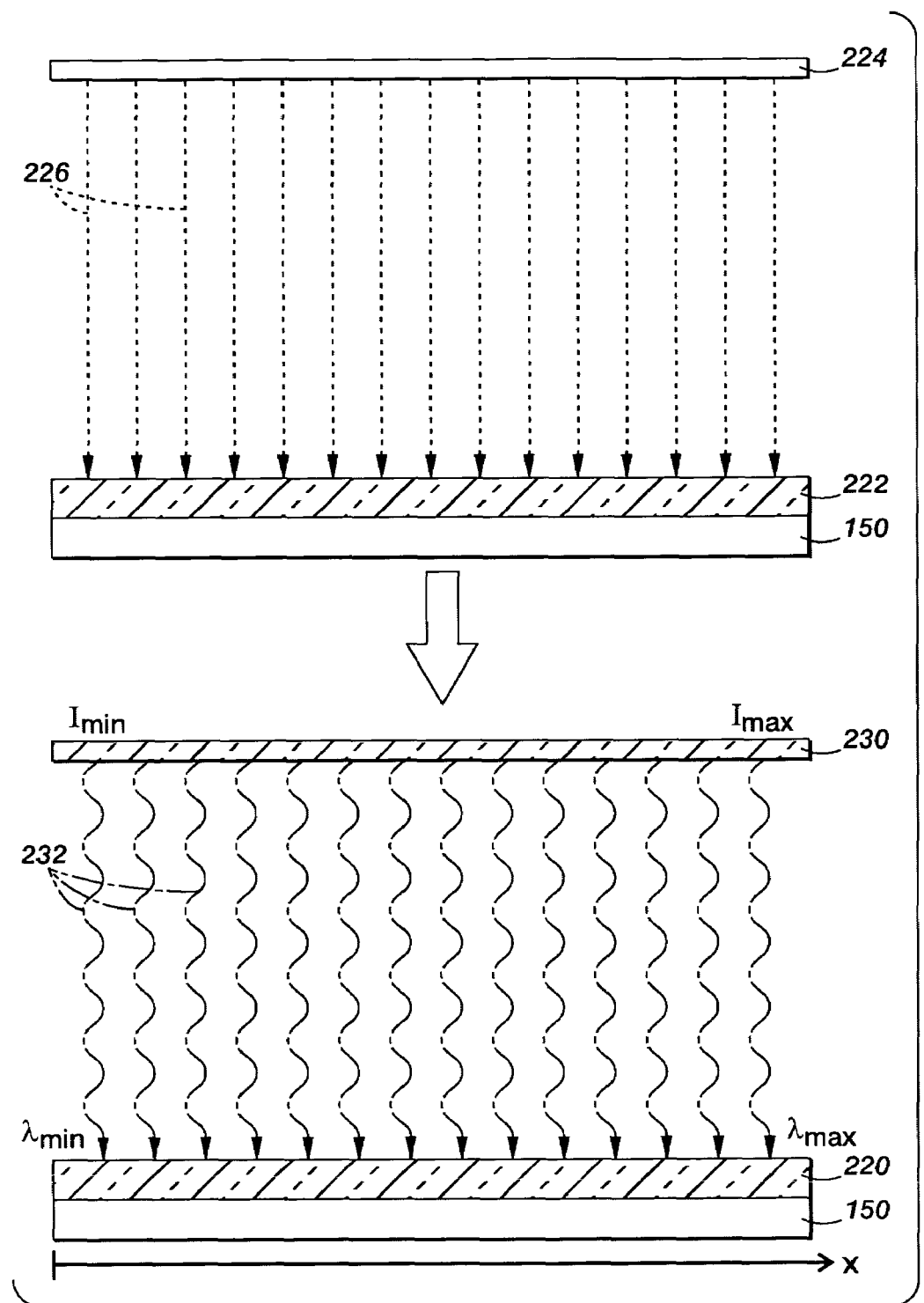
FIG. 9 illustrates another technique for producing a transmission structure that can be used in an assembly in FIG. 2, showing two schematic cross-section views of stages of the technique.

FIG. 9 illustrates a technique that produces transmission structure 220 with laterally varying light transmission properties similar to those illustrated in FIGS. 5 and 7 but without variation in thickness of transmission structure 220. The technique in FIG. 9 can be characterized as providing laterally varying optical thickness d*n, where d is thickness and n is index of refraction, but without actual variation in thickness d. In contrast, the techniques of FIGS. 4-8 provide varying optical thickness by providing actual variation in thickness.

In the upper part of FIG. 9, homogeneous coating 222 is deposited by deposition source 224, which provides deposition beam 226 uniformly over the surface of photosensor array 150 similar to those in FIGS. 4, 6, and 8. This operation could, for example, be implemented with conventional deposition techniques.

Then, in the lower part of FIG. 9, light source 230 provides radiation 232 that is scanned across the coating over array 150 to introduce a laterally varying change of refractive index in resulting transmission structure 220. For example, source 230 can be an ultraviolet source that provides intensity I with a constant value along each line parallel to the y-axis (perpendicular to the plane of FIG. 9), but varying from $I_{min}$ for lines nearer the y-axis to $I_{max}$ for lines farther from the y-axis, as shown in FIG. 9 by the values along the x-axis. As a result, the wavelengths transmitted to cells in array 150 can vary along the x-axis from $\lambda_{min}$ to $\lambda_{max}$, as shown. The same pattern of intensity can be concurrently applied by source 230 to each of a number of arrays that are appropriately arranged, allowing batch fabrication of arrays. Two-dimensional variation in optical density equivalent to that in FIG. 8 could also be obtained with two-dimensional variation in the ultraviolet source's intensity.

The techniques illustrated in FIGS. 4-9 could be implemented in various other ways, with different cells of a photosensor array photosensing slightly different subranges of a range of photon energies. For example, additional details about various production and calibration techniques and characteristics of transmission structures that could be employed are described in co-pending U.S. patent application Ser. No. 10/922,870, entitled "Chip-size Wavelength Detector" and incorporated herein by reference in its entirety. Also, co-pending U.S. patent application Ser. No. 11/316,241, entitled "Photosensing to Obtain Information From Photon Energies" and Incorporated herein by reference, describes a step-like transmission structure that could be used.

The implementations in FIGS. 1-9 illustrate examples of apparatus that includes an IC and a relative movement device. The IC includes a photosensor array, and the array includes cells that photosense quantities of photons. The relative movement device produces relative movement between an optical signal and the array, and the optical signal includes photons within an application's range of photon energies. The optical signal follows a path across the array along which it is photosensed by cells in the array. In each of two or more segments of the path, a respective set of cells in the array photosenses the optical signal. Each segment's set of cells photosenses within a respective subrange, and the subranges of at least two of the segments are different from each other.

The implementations in FIGS. 3-9 further illustrate examples of a transmission structure that transmits photons from the optical signal to each segment's respective set of cells. The transmission structure has a series of regions, each of which transmits photons in a respective segment of the path to a respective subset of the cells, and each region transmits within a respective subrange. The respective subranges of at least two of the regions are different.

Finally, implementations of the techniques in FIGS. 1-9 are examples of a detector that detects photon energies emanating from objects. The detector includes a fluidic structure with a set of channels defined therein. Within each channel objects travel while photons emanate from the objects within an application's range of photon energies. The detector also includes an IC that has a photosensor array. The array includes, for each channel, a respective set of cells that photosense objects traveling within the channel. The detector also includes a transmission structure that transmits photons from objects traveling within each of a subset of the channels to the channel's respective set of cells. The transmission structure has a respective series of regions for the channel, and each region transmits photons from objects within a segment of the channel to a respective subset of the channel's set of cells. Each region transmits within a respective subrange, and the subranges of at least two of the regions are different from each other.

If quantities photosensed by the cells are read out in parallel, spectral information about incident photons is obtained. As illustrated in FIG. 3, nearby cells, such as in a parallel row, can photosense quantities of photons throughout the range of photon energies to provide reference information. If adjacent cells in the array have overlapping subranges, computational techniques such as deconvolution can be used to improve accuracy.

In general, the resolution of a technique as in any of FIGS. 4-9 depends heavily on the number of cells in an array, the full width half maximum (FWHM) of the transmission peak, and the peak shift per cell. The smaller the FWHM and the peak shift, the better the resolution. On the other hand, the totally covered spectral width can be enhanced by increasing the FWHM and the peak shift per cell. Therefore, the technique can be customized to the needs of a specific application. For example, the use of a Fabry-Perot cavity as in FIG. 4 enables very high spectral resolution, while a version with multiple cavities and many layers as in commercially available products will be favorable for applications with low light intensities in combination with small spectral resolution such as with fluorescence. With such an approach, the spectral width of the transmission window and the reflectivity of the stop band can be optimized separately, which may be advantageous because the reflectivity of the stop band determines stray light suppression. It would also be possible to use a single laterally graded distributed Bragg reflector (DBR) mirror as in FIGS. 6 and 7 to obtain a photosensor array with high light sensitivity but limited wavelength resolution, appropriate for fluorescence or luminescence sensing.

In a version with only one DBR mirror with slightly graded transmission properties as in FIGS. 6-8, integrated over a photodiode array for example, the photocurrent in each cell is slightly different from its neighbors depending on the incident light spectrum. If the transmission properties of the DBR over each cell are known, the original spectrum of incident light can be reconstructed. The number of cells defines the number of spectral points that can be reconstructed and therefore determines spectral resolution. The reconstruction works best for wavelengths where transmission changes drastically from one cell to the next. Therefore, this technique could be used to resolve wavelengths at the edges of the DBR mirror. The DBR mirror could be positioned in such a way that the side edges on one side cover the spectral region being analyzed. Multiplication of the resulting photocurrent with a matrix that contains the transmission function of the DBR mirror provides a reconstruction of the incident light spectral distribution.

Resolution can be improved by positioning DBRs on a second row of the photodiode array so that the opposite edge of the reflectivity plateau overlaps the spectral range of interest. Once again, to evaluate the data, the total light intensity distribution must be known for all cells, which can be obtained from a third row of pixels without any DBRs.

A particular advantage of analyzer 10, when implemented with techniques similar to those of FIGS. 3-9, is that spectral information of objects can be collected step-by-step as the objects move across or along a series of sensing components, each of which obtains information about a respective range of photon energies. As a result, highly sensitive optical characterization techniques can be combined, including multiple range fluorescence spectroscopy and Raman spectroscopy, as described above in relation to FIG. 1. Each of sensing components 56, 58, and 60 can be thought of as a chip-size spectrometer that includes a photosensor array together with a laterally varying filter such as a coating. The laterally varying transmission and reflection properties of the coating over the photosensor array define a correlation between position and photon energy. Therefore the spatially dependent signal from the photosensor array contains information about the incident spectrum. Because of the distributed nature of the spectrometer and the fact that the incident light traverses the photosensor array in the process of resolving spectral distribution, sensitivity is improved, making additional optics unnecessary.

Relative movement between an object and a photosensor array can be obtained in various ways, such as by moving one or both of the object and the array. Movement of an object can be guided in various ways, including by falling through a funnel under gravitational acceleration; by being injected into a well-defined stream of air, liquid, or other particles; or by being guided by a tube, capillary, or similar aperture.

In general, high sensitivity is obtained by the above techniques because the light from the object is received at any given time by only a few cells with relatively narrow subranges. But by photosensing light emanating from an object or another optical signal across the entire array, information about a complete range of photon energies can obtained. This technique therefore allows longer integration times than conventional techniques but does not sacrifice throughput capacity. Sensitivity can be adjusted by selecting the size and number of cells assigned to a specific subrange of photon energies. Simpler optics can be used and no dispersion element is necessary. Note that in conventional spectrometers, any light that is diffracted into the $0^{th}$, $2^{nd}$, and higher orders is wasted.

In experimental implementations, a coating as in FIG. 4 typically transmits approximately 60% of photons in its respective subrange. The subranges can be chosen with wavelengths that span between 0.01 and tens of nanometers (nm), depending on the design and gradient of the coating and the cell size of the photosensor array. Very high light yield can be achieved by using a highly sensitive photosensor, such as an avalanche photosensor array.

In contrast to transmission structures 160, 180, 210, and 220, any coating or other transmission structure over row 102 in FIG. 3 must function as a gray filter across the range $\lambda_{all}$ in order to provide a suitable reference. It may also be possible to leave row 102 uncoated in some implementations.

Figure 10:
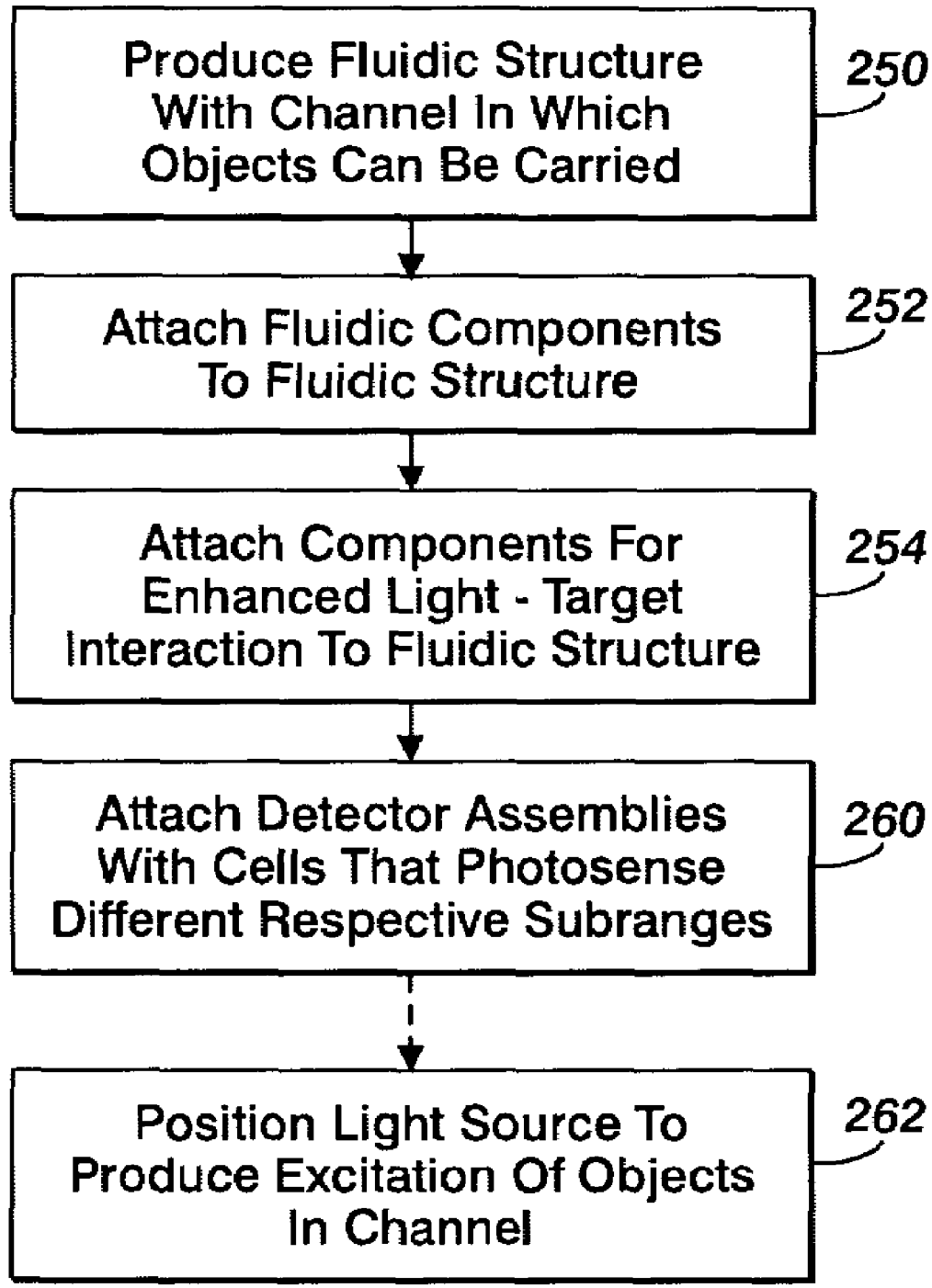
FIG. 10 is a flowchart showing general operations that can be performed in producing an analyzer as in FIG. 1.

FIG. 10 illustrates exemplary operations in producing an analyzer like analyzer 10 in FIG. 1. In particular, the operations in FIG. 10 make it possible to produce apparatus in which relative movement between an optical signal and a photosensor array can be produced, and in which, for different segments of the optical signal's path across the array, respective sets of cells photosense within different respective subranges of photon energy.

The operation in box 250 in FIG. 10 produces a fluidic structure with a channel in which objects can be carried by fluid. For example, the operation in box 250 could include manufacturing a fluidic structure by positioning or otherwise producing a structured spacer layer between two quartz slides. The spacer layer could be a patterned layer of PDMS, produced as described above in relation to FIG. 2, or could be any other suitable material or combination of materials, including, for example, Gelfilm® or quartz. The operation in box 250 could alternatively be implemented in various other ways, such as by defining a fluidic channel in a quartz slide by glass etching or by molding PDMS to produce a channel, and by then combining the resulting structure with an upper quartz slide. In another alternative, two layers of PDMS could be fabricated on separate substrates and then one could be flipped over and aligned with the other by chip-on-chip assembly. Also, a final substrate of glass, PCB, or PDMS or sufficient hardness could be used to allow direction connection to control and detection measurement circuitry.

The operation in box 252 then attaches fluidic components to the fluidic structure produced in box 250. The fluidic components attached in box 252 can include, for example, connectors, tubing, pumps, sensors and so forth. An important function of the fluidic components attached in box 252 is that they can be operated to cause and control movement of objects in the channel. The operation in box 252 can also include attaching wires or other appropriate circuitry to provide signals from a microprocessor or input/output (I/O) device to pumps and other fluidic components.

The operation in box 254 attaches components for enhanced light-target interaction. In the implementation described above in relation to FIGS. 1 and 2, for example, the operation in box 254 can attach optical component 96 on the side of support layer 90, providing an appropriate surface through which light can be coupled into a portion of channel 14 that functions as an anti-resonant waveguide. Similarly, the operation in box 254 can produce spacers 72 to provide a suitable gap that avoids interference with anti-resonant wave guiding; because of spacers 72, when the IC in detector 87 is later attached with gap 88 between it and the fluidic structure, the IC does not interfere with propagation of light in channel 14. For other techniques to produce enhanced light-target interaction, other suitable components can be attached to the fluidic structure.

The operation in box 260 attaches photosensor arrays with cells that photosense in different subranges. The operation in box 260 can be implemented by attaching a structure like any of the above-described implementations of detector 87. The detector can also include reference cells, which could be produced as described in more detail in co-pending U.S. patent application Ser. No. 11/316,438, entitled "Photosensing Throughout Energy Range and in Subranges", and incorporated herein by reference in its entirety. The operation in box 260 can also include attachment of wires or any other appropriate form of circuitry such as to provide power and permit a microprocessor or I/O device to read out information from the cells of each photosensor array.

The operation in box 262 can be performed at a different time, as suggested by the dashed line. For example, it could be performed in box 254, or it could be done later, because it is necessary more for operation of the analyzer than for its production. Like the detector, each light source can be attached once, after which it is stationary. In the operation in box 262, one or more light sources are positioned to produce excitation of objects being carried within the channel. For example, the operation in box 262 could include attaching and/or aligning a laser, an LED array, or other light source so that its light is coupled into a portion of the channel functioning as an anti-resonant waveguide. The operation in box 282 can also include attaching wires or other appropriate circuitry to provide signals from a microprocessor or I/O device to light sources.

The technique of FIG. 10 could be modified in many ways within the scope of the invention. For example, the operations in boxes 252, 254, and 260 could be combined in any appropriate way to facilitate attachment of components in a desired sequence. Also, an additional operation could be performed to align or attach interconnects between ICs, gates, and other circuitry, such as connectors to a microprocessor or computer, or this operation could be partially performed in each of boxes 272, 274, 280, and 282. Furthermore, the technique of FIG. 10 is extremely general, and could be employed to produce a wide variety of different fluidic structures with enhanced light-target interaction, detectors, and movement of fluids and objects that emanate light. The example illustrated in FIGS. 1 and 2, above, shows how objects carried through a channel can pass through a series of sensing components, each of which includes a respective detector with its own photosensor array, but various other arrangements are possible, examples of which are described below.

Implementations of FIG. 10 illustrate examples of methods that produce a detector with an IC and a relative movement device. The IC includes a photosensor array with cells that photosense quantities of photons received. The relative movement device produces relative movement between an optical signal and the photosensor array, and the optical signal follows a path across the array along which cells photosense the optical signal. These methods produce the detector so that each of two or more segments of the path has a respective set of cells in the array. Each segment's set of cells photosenses within a respective subrange of the optical signal's range of photon energies, and the respective subranges of at least two of the segments are different from each other.

FIG. 11 shows an alternative arrangement that could be produced by an implementation of FIG. 10, with components similar to those described above in relation to FIG. 1 having the same reference numerals. As in FIG. 1, first and second fluorescence sensing components 56 and 58 are next to each other in the series of sensing components along channel 14. In addition, however, they are positioned so that IC 270 can be attached over both of them. As a result, the photosensor array of IC 270 includes both cells along channel 14 within component 56 and also cells along channel 14 within component 58. In other respects, the operation of IC 270 can be the same as described above.

FIG. 12 is a cross-section along the line 12-12 in FIG. 11, and shows how detector 272, which includes IC 270, can be supported over air gap 88 by spacers 72 in the same manner described above in relation to FIGS. 1 and 2. In general, detector 272 can include any of the features described above in relation to FIGS. 3-9, but the lateral variation in optical thickness of the transmission structure may be such that the ranges and subranges photosensed within sensing component 56 are different from those photosensed within sensing component 58; alternatively, the ranges and subranges could be the same. An additional important feature is that spacers 72 can help to reduce cross-talk between components 56 and 58 because spacers 72 can be shaped and positioned to act as light-absorbing walls between the two components. In other words, those of spacers 72 that are between components 56 and 58 prevent photons emanating from channel 14 underneath component 56 from propagating to cells of component 58 and vice versa.

FIG. 13 shows an alternative arrangement in which detector 272 as in FIG. 12 is positioned over a set of parallel channels 274, which could be produced by producing walls 276 to subdivide a larger channel into subchannels. An advantage of the technique illustrated in FIG. 13 is that several streams of objects can be analyzed in parallel in order to increase throughput or specificity of an analyzer. As mentioned above in relation to FIGS. 11 and 12, laterally varying optical thicknesses of a transmission structure can be produced so that a different range of photon energies is photosensed in each of channels 274, or different subranges are photosensed in different channels, or the same ranges and subranges could be photosensed in all channels.

FIG. 14 shows an alternative arrangement that could be produced by an implementation of sensing component 58 in FIG. 2, with components similar to those described above in relation to FIG. 2 having the same reference numerals. As in FIG. 2, portion 80 of channel 14 functions as an anti-resonant waveguide in response to light from source 84. Assembly 87 is along portion 80, separated from plate 94 by spacers 72. Upstream from portion 80 (but downstream from light source 84) can be positioned a series of triggering photodetectors, with photodetector 290 on spacers 292 illustratively representing the series. Alternatively, another type of detector could be used, such as a Coulter counter or Mie scatter sensor.

Within portion 80, fluorescing objects 300, 302, and 304 are being carried through channel 14. As they fluoresce, objects 300, 302, and 304 emanate photons, represented respectively by rays 310, 312, and 314. As described in greater detail below, quantities read out from a photosensor array in detector 87 can be used to obtain information about objects 300, 302, and 304 even though all three objects are concurrently traveling past the array.

Figure 15:
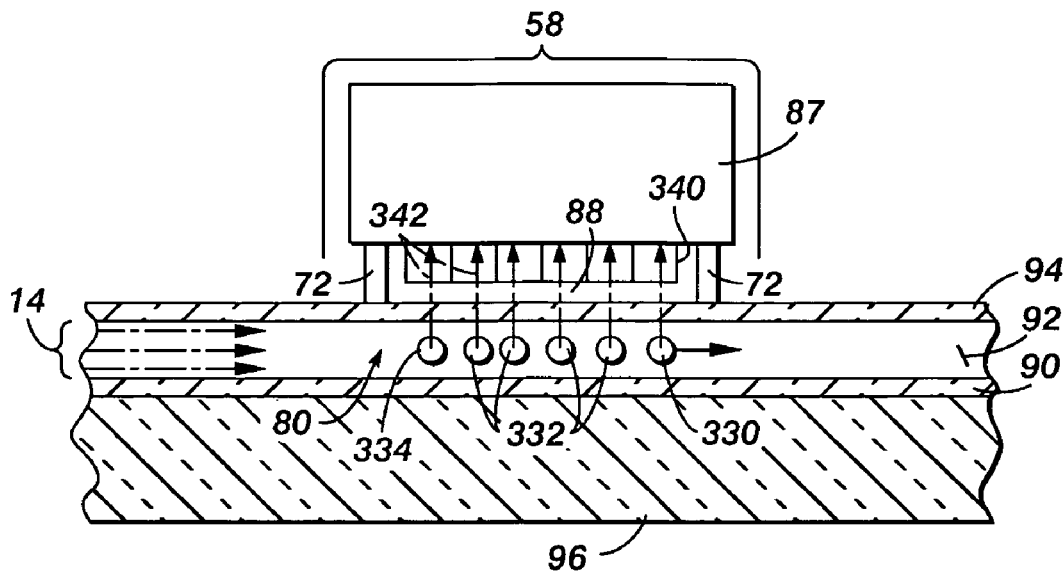
FIG. 15 is a schematic cross-sectional view of an alternative implementation to that of FIG. 14.

FIG. 15 shows an alternative to the implementation of sensing component 58 in FIG. 14, with similar components having the same reference numerals. As in FIG. 14, portion 80 of channel 14 functions as an anti-resonant waveguide in response to light from a source (not shown). Assembly 87 is along portion 80, separated from plate 94 by gap 88 due to spacers 72. Upstream from portion 80 (but downstream from light source 84) can be positioned a series of triggering photodetectors (not shown) or, alternatively, another type of detector.

Within portion 80, a closely spaced, continuous sequence of fluorescing objects are being carried through channel 14. FIG. 15 shows a group of the objects passing through portion 80 along assembly 87, and the group is led by object 330 after which follow several intermediate objects 332 and, finally, object 334. As they fluoresce, objects 330, 332, and 334 emanate photons, and the photons pass through optical component 340 attached to assembly 87. Optical component 340 can be implemented, for example, as a Selfoc® lens array similar to lens arrays 164 in FIGS. 4 and 6, as described above. If optical component 340 is present, however, array 164 would be omitted.

As a result of component 340 and as indicated by rays 342, photons emanating from each of objects 330, 332, and 334 are predominantly incident on a different cell of assembly 87 than photons emanating from nearby objects. Therefore, as in FIG. 14, quantities read out from a photosensor array in detector 87 can be used to obtain information about objects 300, 302, and 304 even though a continuous sequence of closely spaced objects is concurrently traveling past the array.

Figure 16:
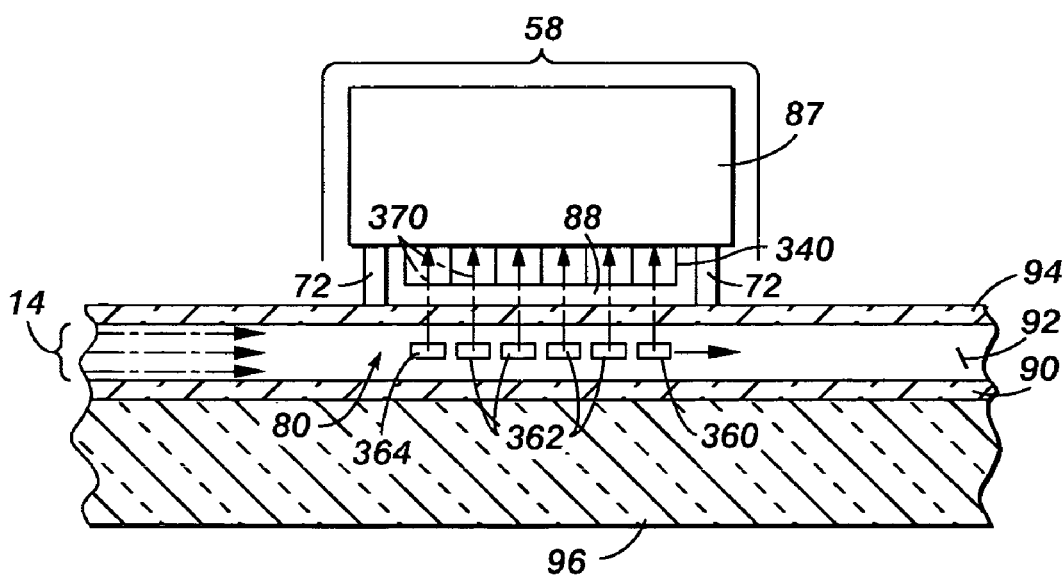
FIG. 16 is a schematic cross-sectional view of another application of the alternative implementation of FIG. 15.

FIG. 16 shows an alternative implementation of structure shown in FIG. 15, with the same structure but without distinguishable objects 330, 332, and 334. In this implementation, fluid flow in channel 14 can be approximated as a continuous sequence of small volumes traveling in channel 14. In effect, the stream of fluid is divided into imaginary small volumes, each of which can be analyzed as if it were an object, allowing for continuous monitoring of how distribution of photon energies emanating from the fluid changes with time, such as due to changing composition of the fluid. In FIG. 16, a group of the small volumes are passing through portion 80 along assembly 87, and the group is led by volume 360 after which follow several intermediate volumes 362 and, finally, volume 364.

Due to interaction with light, particles in volumes 360, 362, and 364 emanate photons, such as due to some combination of fluorescence and scattering by molecules. The distribution of photon energies in each volume depends on concentrations of molecules that are involved in fluorescence and scattering. As in FIG. 15, the photons pass through optical component 340 attached to assembly 87. Rays 370 indicate that photons emanating from each of volumes 360, 362, and 364 are predominantly incident on a different cell of assembly 87 than photons emanating from nearby volumes. Therefore, similarly to FIG. 15, quantities read out from a photosensor array in detector 87 can be used to obtain information about concentrations of molecules in volumes 360, 362, and 364 even though fluid is continuously flowing past the array.

Figure 17:
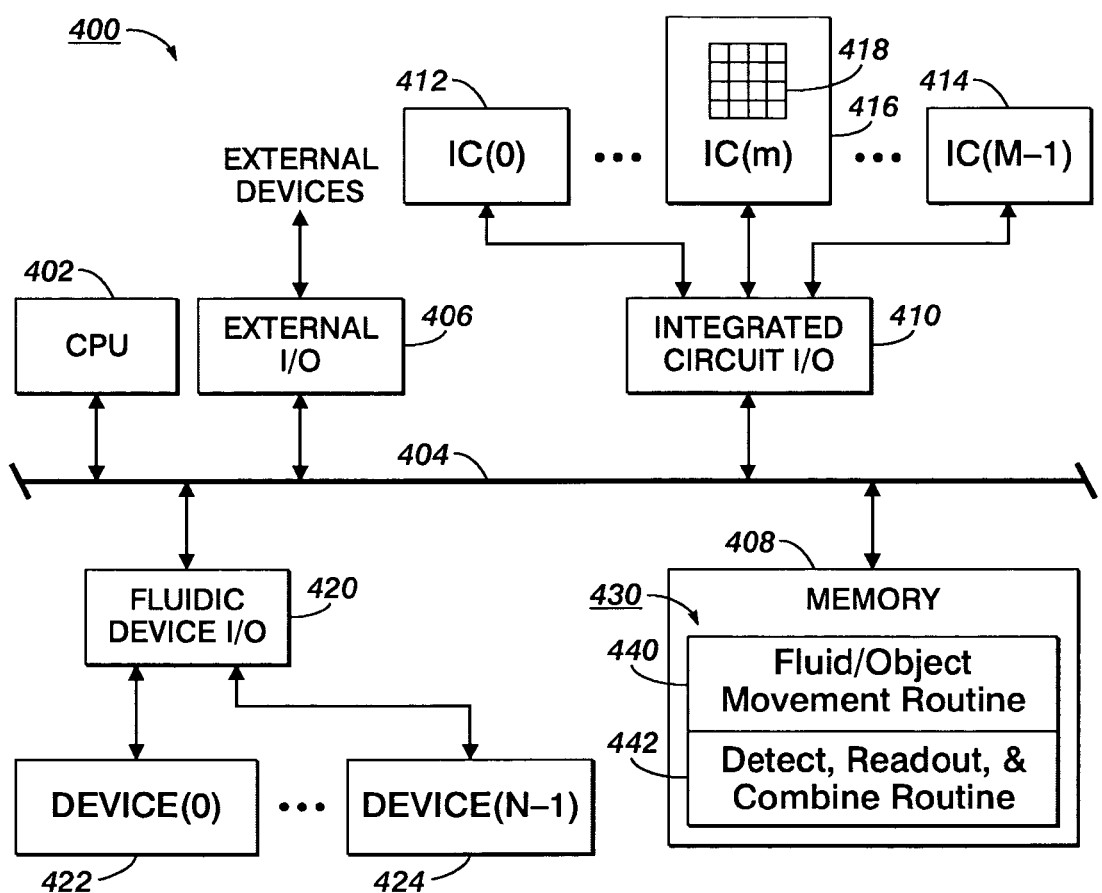
FIG. 17 is a schematic block diagram of a system that can control the analyzer of FIG. 1.

FIG. 17 illustrates system 400, an exemplary system that could be used to operate analyzer 10. Although system 400 illustratively includes central processing unit (CPU) 402 connected to various components through bus 404, a wide variety of other architectures could be employed, including any appropriate combination of hardware and software, as well as specialized hardware components such as application specific integrated circuits (ASICs) for one or more of the illustrated components or in place of a software component executed by CPU 402.

System 400 also includes external input/output (I/O) component 406 and memory 408, both connected to bus 404. External I/O 406 permits CPU 402 to communicate with devices outside of system 400.

Additional components connected to bus 404 are within or connected to analyzer 10. In the illustrated implementation of system 400, IC I/O 410 is a component that permits CPU 402 to communicate with ICs in analyzer 10, such as the various ICs, photodetectors, and other sensing components described above; M ICs are illustrated in FIG. 17 by a series extending from IC(0) 412 to IC (M-1) 414. ICs 412 through 414 illustratively include IC(m) 416 with a photosensor array 418, which includes cells that photosense subranges as described above. Similarly, fluidic device I/O 420 is a component permitting CPU 402 to communicate with various fluidic devices such as pumps, metering electrodes, smart gates and other devices for gating and bifurcating, valves, flow or pressure sensors, and so forth; N fluidic devices are represented in FIG. 17 by device (0) 422 through device (N-1) 424. Such devices could be implemented in various ways; smart gates, for example, could be implemented with MEMS style microgates or by using electromagnetic forces, which are effective because most particles are charged such that an electric field can be used to direct them as desired in a channel.

Memory 408 illustratively includes program memory 430 although instructions for execution by CPU 402 could be provided in various other forms of software or hardware, on or off of CPU 402. The routines stored in program memory 430 illustratively include fluid/object movement routine 440 and detect, readout, and combine routine 442. In addition, program memory 430 can also store a number of subroutines (not shown) that CPU 402 can call in executing routines 440 and 442.

CPU 402 executes fluid/object movement routine 440 to communicate with fluidic devices 422 through 424. For example, CPU 402 can receive signals from sensors, perform computations to determine what fluidic operations are necessary, and then provide signals to activate pumps, metering electrodes, gates, and valves to produce appropriate movement of fluid and of objects carried by fluid in channel 14.

In executing routine 442, CPU 402 can illustratively call a subroutine implemented as shown in FIG. 18, which could instead be within routine 442. The subroutine in FIG. 18 can be implemented for single objects moving past arrays as in FIG. 2; for spaced multiple objects moving past arrays as in FIG. 14; for continuous sequences of objects moving past arrays as in FIG. 15; or for continuous flow of fluid past arrays as in FIG. 16. Also, the subroutine in FIG. 18 follows a general strategy of performing a series of readout operations, after which spectral information is combined and provided, although it would also be possible to provide the information from each readout operation immediately.

When CPU 402 executes the operation in box 480, it performs a pre-sensing readout. The purpose is to obtain information necessary to later perform a sensing readout. The information could be obtained, for example, from a series of photodetectors illustrated by photodetector 290 in FIG. 14 or from reference cells in the photosensor array, such as the cells in row 102 in FIG. 3. It would also be possible to modify the photosensor array to include trigger cells positioned along channel 14 upstream from a line of subrange cells, and uncoated so that they provide information about all photon energies. The operation in box 480 may not be necessary for object-free implementations as in FIG. 16 if information about fluid speed is available from another source (e.g. the pump speed). If necessary, additional well-known techniques for measuring fluid velocity may be used to trigger sensing.

Using the information from box 480, CPU 402 can obtain information about each object or small volume and determine an appropriate sensing period for each object or volume, in the operation in box 482. For example, CPU 402 could perform calculations to determine whether one or more objects are present, the position of each object, and the speed of each object; in object-free implementations as in FIG. 16, CPU 402 may need only determine the fluid speed. Using this information and taking into account previously calculated sensing periods for the same objects or for similar fluid volumes, if any, CPU 402 can also determine an appropriate sensing period to be used during sensing readout; in general, the sensing period must provide an integration time shorter than the time necessary for an object or small volume to pass each subrange cell. Each object or small volume can therefore have a unique sensing period. Alternatively, CPU 402 could provide signals to adjust fluid speed to obtain the same result.

CPU 402 can then perform the sensing readout operation, in box 484. This operation includes providing signals so that photons are photosensed cumulatively during the sensing period obtained in box 482, and may also include signals to peripheral circuitry on an IC so that analog quantities photosensed by subrange cells are adjusted based on analog quantities sensed by paired reference cells. After adjustment, if any, analog quantities can be converted to digital signals for readout. The operation in box 484 can be implemented in whatever manner is appropriate for a given IC, whether a CCD or CMOS implementation, and regardless of whether readout is purely serial or is also parallel.

The photosensed quantities read out in box 484 can also be digitally adjusted by CPU 402 before being stored for each object or small volume, in box 490. The digital adjustment can include adjusting quantities photosensed by subrange cells based on quantities photosensed by paired reference cells, and can also include any necessary adjustments due to differences in sensing periods or other factors. The digital adjustment in box 490 and the analog adjustment, if any, in box 484 can employ the techniques described in co-pending U.S. patent application Ser. No. 11/316,438, entitled "Photosensing Throughout Energy Range and in Subranges", and incorporated herein by reference in its entirety. The position and speed information about each object or small volume from box 482 can be used to determine which photosensed quantities result from photons emanating from each object or small volume.

Although described in relation to the implementations in FIGS. 1-17, the operations in FIG. 18 could be modified for other implementations. For example, even if several objects are emanating photons to the same cell at the same time, it may be possible to perform computational algorithms to separate the signals of the objects. Also, in analyzing optical signals emanating from a continuous fluidic stream without distinguishable objects in it as in FIG. 16, each imaginary small volume can be analyzed as if it were one or more objects, allowing for continuous monitoring of how distribution of photon energies from the fluid changes with time, such as due to changing composition of the fluid.

In performing the operations in boxes 482 and 490, CPU 402 can employ data structures (not shown) stored in memory 408. For example, one data structure can store each object's or small volume's previously calculated position and speed, which can then be used in performing subsequent calculations to identify the same object or small volume. Also, a readout data structure can be employed to hold all of the adjusted quantity information about each object or small volume. The operation in box 490 can update the readout data structure each time it obtains additional information about the same object or small volume. In an implementation as in FIG. 17, the operations in boxes 480, 482, 484, and 490 can be performed separately for each of ICs 412 through 414. Further, as suggested by the dashed line from box 490 to box 480, the same operations can be performed repeatedly for each of the ICs. If the objects or small volumes can be correctly identified throughout channel 14, the readout data structure can be used to hold all of the information obtained from all ICs.

Between consecutive executions of the operations in boxes 480, 482, 484, and 490, each object's optical signal may move only a few cells along the photosensing path, and some implementations may require that consecutive objects be sufficiently separated to avoid confusion. For example, each object may be a few μm in diameter, each pixel may have a length along the photosensing path of between 10 and 20 μm, and consecutive objects may be two or three cell lengths apart. For larger objects or for cells of different sizes, the spacing between consecutive objects can be adjusted appropriately.

As can be understood, only a small fraction of an application's range of photon energies is photosensed and stored at a time by the operation in box 490. As the operations in boxes 480, 482, 484, and 490 are repeated while an object or small volume travels along the path past the array, more and more spectral intervals are resolved. When the object or small volume has passed the whole array, its spectral information can be recomposed from the stored fractions.

Upon completion of any suitable amount of information gathering in boxes 480, 482, 484, and 490, CPU 402 can perform the operation in box 492 to provide photosensed quantities, such as in the form of data for another routine or as output through external I/O 406. As shown, this operation can include combining the sensed quantities for each object or small volume so that spectral information about the object or small volume can be provided, such as in the form of a profile or other data structure.

The implementations of the techniques illustrated in FIGS. 1-18 illustrate examples of a method of optical sensing, which can be implemented as a method of using a sensor. The method causes photons having energies within a range of photon energies to emanate from a fluid moving in a flow direction through a channel or channel portion within a fluidic structure. The method uses two or more sets of cells to photosense the emanating photons, and the sets of cells can be positioned in a series that extends in the flow direction along the channel. The sets of cells can be in a photosensor array included in an IC. Each set of cells photosenses within a respective subrange, and the subranges of at least two of the sets of cells are different from each other.

In specific implementations of FIGS. 1-18, the photons emanate from volumes of the fluid or from objects being carried by the fluid, in which case the objects may be excited to cause emission or may be illuminated to cause scattering. The objects can be droplets with fluorescent components or with scattering components, or may include analytes of some type. The photosensed quantities can be used to produce signals indicating spectral information about photons from an object.

Implementations of FIGS. 1-18 also illustrate examples of sensors that include a fluidic structure and an IC. Photons having energies within a range of photon energies can emanate from the fluid moving in a flow direction through each channel portion within a fluidic structure, and two or more sets of cells in a photosensor array in an IC can photosense the emanating photons. The sets of cells for each channel portion are positioned in a series that extends in the flow direction along the channel portion, and each set of cells photosenses within a respective subrange.

In specific implementations, the channel portions are portions of a single channel or portions of different channels. A sensor can include a transmission structure that transmits photons to each series of cells from the respective channel portion, with each region of the transmission structure transmitting photons within a respective subrange. The transmission structure can be a continuously varying coating over the photosensor array. Apparatus can include the sensor and a propulsion component that can propel fluid. A system can include the sensor and also a processor connected to read out photosensed quantities.

Implementations of FIGS. 4-10 illustrate examples of a method of producing a sensor as described above.

Implementations of FIGS. 1-18 also illustrate examples of a method of detecting photon energies emanating from objects. The method causes one or more objects to travel along a path while photons within a range of photon energies emanate from the objects. Along each of two or more segments of the path, the method photosenses quantity of a respective subset of photons from the objects using a respective set of cells in a photosensor array included in an IC. The subset of photons of each segment are within a respective subrange, and the respective subranges of at least two of the segments are different from each other.

In specific implementations of FIGS. 1-18, objects are caused to travel by being conveyed in a fluid. Also, one object at a time can be caused to travel through the segments of the path so that the sets of cells photosense photons from one object at a time. The photosensor array can be along a series of segments, and two or more objects at a time can be caused to concurrently travel through the series of segments so that different sets of cells in the array can concurrently photosense quantities of photons from respective objects. In addition, a method implemented as in FIG. 18 can obtain information about an object's position and speed and then perform photosensing based on the information. Components of the objects can be excited, causing the objects to emit photons, or the objects can be illuminated, causing them to scatter photons.

The implementations in FIGS. 1-18 also illustrate examples of a sensor that includes an object movement device and a photosensor array included in an IC. The object movement device causes objects to travel along a path while photons emanate, as described above. Along each of two or more segments of the path, the array includes a respective set of one or more cells that photosense quantity of a respective subset of photons in a respective subrange as described above.

In specific implementations, the object movement device can include a fluidic structure and objects can travel within a channel defined in the fluidic structure. A sensor can include a transmission structure that transmits photons from each segment of the path to the respective set of cells, with each region of the transmission structure transmitting photons within a respective subrange. The transmission structure can be a continuously varying coating over the photosensor array. A system can include the sensor and also a processor connected to read out photosensed quantities from the photosensor array.

Techniques involving emanation of light from channels or from objects and photosensing in subranges, as exemplified by the implementations in FIGS. 1-18, can also be applied in other applications.

Various of the techniques described above have been successfully implemented or simulated, including the production of a detector that includes a commercially available IC covered with a laterally graded Fabry-Perot cavity filter on a glass slide. Wavelength resolution has been experimentally determined and successfully simulated on a computer. Anti-resonant waveguide techniques have been successfully tested.

The exemplary implementations described above are advantageous because they can provide compact, inexpensive components that generally require no additional mechanical or optical parts to perform functions such as spectrometry. For example, a portable, easy-to-use spectrometer could include an analyzer as described above; a portable, compact unit could, for example, be standard equipment for emergency response teams anywhere. The results of photosensing can be read out rapidly and in parallel from a number of ICs, allowing fast data acquisition; as a result, an initial characterization of an object may be used to determine whether to perform more refined or detailed analysis of the object, or to determine which of different types of analysis are performed. A multi-signal approach like this is compatible with reagent-less identification, i.e. without specific binding, tagging, labeling, dyes, or stains; also, a wide variety of objects can be identified in a wide variety of fluids, such as various nanoparticles, microorganisms, bioagents, and toxins in various aerosols, water, blood, food, and other specimens.

A number of ICs may be used to address a wide range of photon energies by using suitable coating materials, possibly ranging from the ultraviolet to the far infrared and even into the terahertz range. The ICs can be integrated into complex systems, such as fluidic systems, and may be employed for multiple functions, possibly including both spectrometry and wavelength shift detection. The ICs are especially useful in spectrometry applications in which light cannot be spread homogeneously over a photosensor array, because nearby reference cells can be used to normalize or otherwise adjust sensed quantities.

Spectrometry measurements have a wide variety of applications, including, for example, optical instrumentation, telecommunications, fluorescence devices, process control, optical signal scanning, detection systems for chemical and biological agents, and so forth. An example of a specific application is an in-line detector for manufacturing and functionalizing colloidal particles in an industrial setting. In this application, processes typically are performed in closed systems and the properties of colloidal particles can be assessed only after all processing steps are completed. A small detection platform implemented as described above can be easily built into an on-line detector directly connected to a manufacturing vessel. As a result, small amounts of particles can be analyzed continuously in real time to determine size, chemical composition, and surface conditions. This approach permits instant process adjustments leading to production of materials with consistent properties from run to run. In-line Coulter counters for instant size measurements are already commercially available, but compact detectors as described above can also probe chemical composition using multiple advanced spectroscopic methods, an approach not previously available.

Various specific spectroscopic techniques can be implemented with the techniques described above, including absorption spectroscopy (e.g. gas sensing), fluorescence spectroscopy, and Raman spectroscopy, all of which are discussed above. The techniques described above, however, are not limited specifically to spectroscopy, but could also be applied in other photosensing situations. Additional description of applications in which photon energy is sensed is found in co-pending U.S. patent application Ser. No. 11/315,992, entitled "Sensing Photons Energies of Optical Signals", and incorporated herein by reference in its entirety.

The exemplary implementations described above generally rely on transmission structures that include highly reflective interfaces, so that much of the incident light is reflected and only a small fraction reaches the photosensor array. Therefore, the techniques described above are especially useful in applications in which light intensity is very high or a light source emits through a large area or over an extended time. In addition, the above techniques make it possible to increase sensitivity by choosing very long integration times (without loss of throughput capacity), simpler optics, and no dispersion element. By contrast, some conventional systems such as monochromators lose all light defracted into the $0^{th}$, $2^{nd}$, and higher orders. In the implementations described above, very high light yield can be achieved by combining a transmission structure with a highly sensitive photosensor array, such as one that includes avalanche photodetectors.

In addition, components could have various shapes, dimensions, or other numerical or qualitative characteristics other than those illustrated and described above. For example, in the exemplary implementations described above, cells of a photosensor array photosense in different subranges of an application's photon energy range. The subranges of cells could have any appropriate widths and relationships, and could, for example, overlap or be distinct. The width of a cell's subrange can be chosen by designing the transmission structure and the cell sensing area; for example, the width may be as small as 0.1 nm or as great as tens of nanometers.

Some of the above exemplary implementations involve specific materials, such as in fluidic structures, photosensor arrays, and transmission structures, but the invention could be implemented with a wide variety of materials and with layered structures with various combinations of sublayers. In particular, photosensor arrays for a desired speed, sensitivity and wavelength range could have any suitable material, such as silicon, germanium, indium-gallium-arsenide, gallium arsenide, gallium nitride, or lead sulphide, and could be produced with any appropriate kind of devices, including, for example, photodiodes, avalanche photodiodes, p-i-n diodes, photoconductors, and so forth, with any appropriate technique for sensing and reading out information whether based on CCD, CMOS, or other techniques. Various commercially available detector arrays have pixel densities as high as ten megapixels, and some high density ICs have become relatively inexpensive.

Similarly, transmission structures could be fabricated with any appropriate techniques, including thin film technology such as sputtering, e-beam or thermal evaporation with or without plasma assistance, epitaxial growth, MBE, MOCVD, and so forth. To produce Bragg mirrors, appropriate pairs of materials with low absorption coefficients and large difference in refractive indices could be chosen, bearing in mind the photon energies of interest; exemplary materials include $SiO_2/TiO_2$, $SiO_2/Ta_2O_5$, GaAs/AlAs, and GaAs/AlGaAs. Thicknesses of layer in transmission structures may vary from 30 nm up to a few hundred nanometers.

Some of the above exemplary implementations involve particular types of transmission structures, such as Bragg mirrors and paired distributed Bragg reflectors separated by a Fabry-Perot cavity, but these transmission structures are merely exemplary, and any transmission structure that has laterally varying optical thickness could be used. Various techniques could be used to produce transmission structures with lateral variation in addition to those described above, including, during deposition, tilting the substrate, using a shadow mask, or using a temperature gradient to obtain graded layer thickness; also, during homogeneous deposition, off-axis doping, such as by e-beam, MBE, or MOVPE, could produce lateral variation.

Furthermore, various techniques other than transmission structures could be used to obtain photosensor arrays in which cells sense different subranges of photon energy.

Some of the above exemplary implementations employ an arrangement of ICs relative to fluidic structures in which fluid moves and may carry objects, and a wide variety of such arrangements, with or without fluidic structures, could be made within the scope of the invention. The invention could also be implemented with any other suitable type of photosensor array, including simple light-to-electric signal transducers arranged as cells of a photosensor array. Although objects could be photosensed one at a time, the techniques described above also allow concurrent photosensing of multiple objects or even photosensing of volumes of fluid that do not contain distinguishable objects. In one example, a preliminary inspection of an analyte could be made with an IC with a 400-700 nm laterally varying filter to detect fluorescence or scattering in the 400-700 nm range, after which a more refined inspection could be made with another IC, such as to perform Raman spectroscopy in the range of 100 $cm^{-1}$ to a few 1000 $cm^{-1}$. Rather than using separate ICs, different rows of a single two-dimensional photosensor array on an IC could be differently coated to photosense in different ranges. Techniques as described above might also be combined with relative movement techniques as described in co-pending U.S. patent application Ser. No. 11/315,926, entitled "Sensing Photon Energies of Optical Signals" and incorporated herein by reference in its entirety.

Some of the above exemplary implementations employing fluidic structures also employ enhanced light-target interaction to obtain fluorescence. In general, however, the techniques described above could also be used for self-emitting or auto-fluorescing objects such as particles. Furthermore, various types of fluorescence, photo-luminescence, chemo-fluorescence, inelastic scattering, and so forth could be employed. The technique of anti-resonant waveguiding, described above, is only one of many techniques that could be used for enhanced light-target interaction, and any such excitation technique could be applied continuously or intermittently along a path. Various parameters could be adjusted to obtain anti-resonant waveguiding, including the shape of quartz or glass surrounding the channel; a thinner structure is generally better, with a surface parallel to the channel generally being required.

Additional description of excitation techniques is found in co-pending U.S. patent application Ser. No. 11/316,660, entitled "Providing Light to Channels or Portions" and co-pending U.S. patent application Ser. No. 11/315,992, entitled "Sensing Photons from Objects in Channels", both of which are incorporated herein by reference.

The exemplary implementation in FIG. 17 employs a CPU, which could be a microprocessor or any other appropriate component. In general, routines as described above in relation to FIGS. 17 and 18 could be done either on the same IC as a photosensor array, on other components, or on a combination of the two, with any appropriate combination of software or hardware.

The above exemplary implementations generally involve production and use of photosensor arrays, ICs, transmission structures, fluidic structures, sensors, illumination components, optical components, and analyzers following particular operations, but different operations could be performed, the order of the operations could be modified, and additional operations could be added within the scope of the invention. For example, in implementations in which a transmission structure is on a separate substrate from a photosensor array, the transmission structure could be moved relative to the photosensor array between consecutive sensing operations. Also, readout of adjusted or unadjusted sensed quantities from an IC could be performed serially or in parallel, and could be performed cell-by-cell or in a streaming operation.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. A sensor comprising:
    a fluidic structure having defined therein a set of one or more channel portions within each of which fluid can move in a respective flow direction and photons can emanate from the moving fluid, with photons emanating from the moving fluid in each channel portion having energies within a respective range of photon energies; and
    an IC that includes a photosensor array; the array including, for at least one of the channel portions in the set, a respective series of two or more sets of cells; each series extending along the respective channel portion in its flow direction; each set of cells in a channel portion's series being capable of photosensing photons within a respective subrange of the channel portion's range of photon energies; the respective subranges of at least two of the sets of cells being different from each other.

2. The sensor of claim 1, further comprising:
a transmission structure that transmits photons to each series of sets of cells from the respective channel portion; for each series of sets of cells, the transmission structure having a series of regions extending in the respective channel portion's flow direction, each region transmitting to a respective set of the cells photons within a respective subrange of the range of photon energies; the respective subranges of at least two of the regions being different from each other.

3. A method of using the sensor of claim 1, the method comprising:
with fluid moving through one of the channel portions in the respective flow direction, causing photons having energies within the respective range of photon energies to emanate from the moving fluid; and
using two or more of the channel portion's respective sets of cells that have different respective subranges to photosense the emanating photons.

4. The method of claim 3 in which the photons emanate from volumes of fluid or from one or more objects being carried by the moving fluid through the channel portion.

5. The method of claim 4 in which the act of causing photons to emanate includes:
providing excitation to cause emission of photons.

6. The method of claim 5 in which the excitation is provided to droplets that include fluorescent components; in response to the act of providing excitation, the fluorescent components radiating photons within one or more fluorescence subranges of the range of photon energies.

7. The method of claim 4 in which the act of causing photons to emanate includes:
providing illumination to cause scattering of photons.

8. The method of claim 7 in which the illumination is provided to droplets that include scattering components; in response to the act of providing illumination, the scattering components scattering photons within one or more scattering subranges of the range of photon energies.

9. A method of producing the sensor of claim 1, the method comprising:
producing the sensor so that the array includes two or more sets of cells that photosense the emanating photons; the sets of cells being positioned in a series extending in the flow direction along the channel; each set of cells photosensing photons within a respective subrange of the range of photon energies; the respective subranges of at least two of the sets of cells being different from each other.

10. A sensor comprising:
a fluidic structure having defined therein a set of one or more channel portions within each of which fluid can move in a respective flow direction and photons can emanate from the moving fluid or from objects carried by the moving fluid, with photons emanating in each channel portion having energies within a respective range of photon energies;
for one of the channel portions in the set, a respective lens array through which a portion of the photons emanating from the channel portion can pass;
for the one of the channel portions, a respective transmission structure that receives and transmits photons from the respective lens array, the transmission structure having laterally varying transmission properties; and
an integrated circuit (IC) that includes a photosensor array; the array including, for the one of the channel portions, a respective series of two or more sets of cells; the series extending along the one of the channel portions in its flow direction;
the respective lens array and transmission structure of the one of the channel portions being structured so that each of the sets of cells in the respective series receives emanating light from a respective segment of the one of the channel portions; for each of the sets of cells, the transmission structure having a respective region that receives photons from the respective segment through the lens array and that transmits photons to the respective set of the cells, each region transmitting photons within a respective subrange of the range of photon energies of the one of the channel portions; the respective subranges of at least two of the regions being different so that the respective sets of cells photosense photons within different photon energy subranges.

11. The sensor of claim 10 in which the channel portions are portions of a single channel.

12. The sensor of claim 10 in which the channel portions are portions of different channels.

13. The sensor of claim 10 in which the respective transmission structure of the one of the channel portions includes a coating that varies continuously in the flow direction of the channel portion, each respective region including a respective area of the coating.

14. The sensor of claim 13 in which the coating is over the photosensor array.

15. The sensor of claim 10 in which the respective ranges of photon energy of at least two of the channel portions are different from each other.

16. The sensor of claim 10, further comprising:
circuitry that, in response to quantities of photons photosensed by the sets of cells, provides signals indicating spectral information.

17. The sensor of claim 10 in which the IC includes a COD or CMOS photosensor array.

18. Apparatus comprising the sensor of claim 10, the apparatus further comprising:
a propulsion component that can propel the fluid through the one of the channel portions.

19. A system that comprises the sensor of claim 10, the system further comprising:
a processor connected to read out photosensed quantities of photons from the photosensor array.

20. A sensor comprising:
an object movement component that causes objects to travel along a path while photons within a range of photon energies emanate from the objects; and
along the path, a photosensor array included in an IC; along each of two or more segments of the path, the array including a respective set of one or more cells that photosense quantity of a respective subset of photons from the objects; the respective subset of photons of each segment being within a respective subrange of the range of photon energies; the respective subranges of at least two of the segments being different from each other.

21. The sensor of claim 20 in which the object movement component includes a fluidic structure, the object movement component causing the objects to travel within a channel defined in the fluidic structure.

22. The sensor of claim 20, further comprising:
a transmission structure that transmits photons emanating from each segment of the path to the respective set of cells; the transmission structure having a series of regions along the path, each region transmitting photons from a respective segment of the path to the respective set of the cells, each region transmitting to the respective set of the cells photons within a respective subrange of the range of photon energies; the respective subranges of at least two of the regions being different.

23. The sensor of claim 22 in which the transmission structure includes a coating that varies continuously along the path, each region in the respective series of regions including a respective area of the coating.

24. The sensor of claim 23 in which the coating is over the photosensor array.

25. The sensor of claim 20, further comprising:
circuitry that, in response to quantities of photons photosensed by the sets of cells, provides signals indicating spectral information.

26. A system that comprises the sensor of claim 20, the system further comprising:
a processor connected to read out photosensed quantities of photons from the photosensor array.

27. A method of detecting photon energies emanating from objects, the method comprising:
causing one or more objects to travel along a path while photons within a range of photon energies emanate from the objects; and
along each of two or more segments of the path, photosensing quantity of a respective subset of photons from the objects using a respective set of one or more cells in a photosensor array included in an IC; the subset of photons of each segment being within a respective subrange of the range of photon energies; the respective subranges of at least two of the segments being different from each other.

28. The method of claim 27 in which the act of photosensing further comprises, in at least one of the segments of the path:
transmitting only the segment's respective subset of photons from the path to the segment's respective set of cells; and
photosensing quantity of the segment's respective subset of photons transmitted to the segment's respective set of cells.

29. The method of claim 27 in which the act of causing objects to travel comprises carrying the objects in a fluid.

30. The method of claim 27 in which the act of causing objects to travel comprises causing one object at a time to travel through the segments of the path so that the sets of cells photosense quantities of photons from one object at a time.

31. The method of claim 27 in which the photosensor array is along a series of at least two of the segments of the path; the act of causing objects to travel comprising:
causing two or more objects at a time to concurrently travel through the series of segments so that two or more sets of cells in the photosensor array concurrently photosense quantities of photons, each set of cells photosensing photons from a respective one of two or more objects.

32. A method of operating a sensing component that includes:
along each of two or more segments of a path, a respective set of one or more cells in a photosensor array included in an integrated circuit; the method comprising:
causing fluid to travel along the path and causing the fluid or objects carried by the fluid to emanate light within a range of photon energies as the fluid travels along the path;
from each segment of the path, receiving a respective subset of emanating light at a transmission structure that, in response, provides respective output light to the segment's respective set of cells; the subset of light of each segment being within a respective subrange of the range of photon energies; the respective subranges of at least two of the segments being different from each other;
operating each segment's respective set of cells to photosense quantity of the respective subset of output light; and
operating the sensing component to provide output signals based on the photosensed quantities;
the act of causing fluid to travel and causing the fluid or objects carried by the fluid to emanate light comprising at least one of:
causing one light-emanating object at a time to travel through each segment of the path;
causing two or more light-emanating objects to concurrently travel past the photosensor array;
causing a closely spaced, continuous sequence of light-emanating objects to travel past the photosensor array; and
causing a continuous sequence of volumes of fluid to travel past the photosensor array, each volume including light-emanating particles.

33. The method of claim 32, further comprising:
obtaining information about at least one of an object's position and speed;
the act of operating each segment's respective set of cells being performed based on the information.

34. The method of claim 32 in which the act of causing fluid to travel comprises providing excitation to cause emission of photons or providing illumination to cause scattering of photons.

* * * * *